(12) United States Patent
Iyer et al.

(10) Patent No.: US 11,878,049 B1
(45) Date of Patent: Jan. 23, 2024

(54) MITAPIVAT THERAPY AND MODULATORS OF CYTOCHROME P450

(71) Applicant: Agios Pharmaceuticals, Inc., Cambridge, MA (US)

(72) Inventors: Varsha Venkatachalam Iyer, Boston, MA (US); Chandra Agarwal Prakash, North Andover, MA (US); Hua Yang, Acton, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 414 days.

(21) Appl. No.: 16/900,610

(22) Filed: Jun. 12, 2020

Related U.S. Application Data

(60) Provisional application No. 62/861,600, filed on Jun. 14, 2019.

(51) Int. Cl.
*A61K 38/45* (2006.01)
*A61K 45/06* (2006.01)

(52) U.S. Cl.
CPC .............. *A61K 38/45* (2013.01); *A61K 45/06* (2013.01); *C12Y 207/0104* (2013.01)

(58) Field of Classification Search
CPC .......................... A61K 31/4709; A61K 31/496
See application file for complete search history.

(56) References Cited

U.S. PATENT DOCUMENTS

| | | | |
|---|---|---|---|
| 8,785,450 B2 | 7/2014 | Salituro et al. | |
| 2001/0041706 A1 * | 11/2001 | Synold .................... | A61K 45/06 424/736 |
| 2002/0055495 A1 * | 5/2002 | Jannetta .................... | A61P 1/08 514/171 |
| 2010/0331307 A1 * | 12/2010 | Salituro .................... | A61P 9/00 514/218 |
| 2020/0277279 A1 | 9/2020 | Sizemore et al. | |

FOREIGN PATENT DOCUMENTS

| | | | | |
|---|---|---|---|---|
| WO | WO-2012015712 A1 * | 2/2012 | ............. | A61K 38/06 |
| WO | WO-2016/201227 | 12/2016 | | |
| WO | WO-2016201227 A1 * | 12/2016 | ........... | A61K 31/496 |
| WO | WO-2019104134 A1 * | 5/2019 | ........... | A61K 31/496 |

OTHER PUBLICATIONS

Kassa (BMC Hematology pp. 1-11 published 2016) (Year: 2016).*
Chen (Annals of Clinical Microbiology and Antimicrobials vol. 5 pp. 1-11, published 2006) (Year: 2006).*
Anderson, Tools for Purifying the Product: Column Chromatography, Crystallization and Reslurrying. Practical Process Research & Development, 1st Edition. Academic Press, San Diego. Chapter 11, pp. 223-224, (2000).
Barbier et al., American Society of Hematology—57th Annual Meeting. Drive PK: A Phase 2 trial of AG-348 in patients with pyruvate kinase deficiency. Congress Presentation, Dec. 3, 2015, 1 page. (abstract only).
Barbier et al., ENERCA (2015) 6th European Symposium on Rare Anaemias. Activator treatment for pyruvate kinase deficiency—results from phase 1 and overview of phase 2 trial. Congress Presentation, Nov. 21, 2015, 1 page. (abstract only).
Barbier et al., ESH/ENERCA Training Course on Diagnosis and Management of Very Rare Red Cell and Iron Disorders. New treatments of pyruvate kinase deficiency: A Phase 1 multiple ascending dose study of the safety, tolerability, and pharmacokinetics/ pharmacodynamics of AG-348, a first-in-class allosteric activator of pyruvate kinase-R, in healthy subjects. Congress Presentation, Jan. 29, 2016, 20 pages.
Barbier, European Hematology Association—20th Congress. Pyruvate kinase deficiency—clinical development update. Congress Presentation, Jun. 11, 2015, 3 pages.
Berge et al., Pharmaceutical salts. J Pharm Sci. Jan. 1977;66(1):1-19.
Byrn et al., Pharmaceutical solids: a strategic approach to regulatory considerations. Pharm Res. Jul. 1995;12(7):945-54.
Caira, Crystalline polymorphism of organic compounds. Topics in Current Chemistry. Jan. 1998;198:163-208.
CAS Registry No. 2151847-10-6. 8-Quinolinesulfonamide, N-[4-[[4-(cyclopropylmethyl)-1-piperazinyl]carbonyl]phenyl]-, sulfate, hydrate (2:1:3). 1 page, Dec. 5, 2017.
Chen et al., European Hematology Association—20th Congress. Preclinical pharmacokinetic/pharmacodynamic relationships for AG-348, an investigational small-molecule activator of pyruvate kinase. Congress Presentation Poster, Jun. 13, 2015, 1 page.
Chen et al., European Hematology Association—20th Congress. Preclinical pharmacokinetic/pharmacodynamic relationships for AG-348, an investigational smallmolecule activator of pyruvate kinase. Congress Presentation, Jun. 11, 2015, 2 pages. (abstract only).
Chubukov et al., American Society of Hematology—58th Annual Meeting. Characterization of metabolic response to AG-348, an allosteric activator of red cell pyruvate kinase, in healthy volunteers and pyruvate kinase deficiency patients. Congress Presentation Poster, Dec. 5, 2016, 1 page.
Chubukov et al., American Society of Hematology—58th Annual Meeting. Characterization of metabolic response to AG-348, an allosteric activator of red cell pyruvate kinase, in healthy volunteers and pyruvate kinase deficiency patients. Congress Presentation, Nov. 3, 2016, 3 pages. (abstract only).
Clinical & Pharmaceutical Solutions through Analysis—17th Annual Symposium. Metabolic consequences of pyruvate kinase deficiency (PKD), & their correction with AG-348. Congress Presentation, Oct. 2, 2014, 2014, 22 pages.

(Continued)

*Primary Examiner* — Theodore R. Howell
*Assistant Examiner* — George W Kosturko
(74) *Attorney, Agent, or Firm* — McCarter & English, LLP; Michael J. DeGrazia

(57) ABSTRACT

Described herein are methods of treating pyruvate kinase deficiency (PKD), sickle cell disease or thalassemia with mitapivat or a pharmaceutically acceptable salt thereof, or use of the drug for the treatment of these conditions, in combination with or in the absence of with a secondary drug, such as an inducer or an inhibitor of cytochrome P450. Various doses and dosing regimens of mitapivat in monotherapy and in concomitant medications are described.

19 Claims, 4 Drawing Sheets

(56) References Cited

OTHER PUBLICATIONS

Clinical & Pharmaceutical Solutions through Analysis—3rd Annual Metabolomics Symposium. Using metabolism to support drug discovery: from target identification to biomarker validation. Congress Presentation, Feb. 27, 2017, 22 pages.
Glenthoj et al., European Hematology Association Scientific Working Group—2019 Scientific Meeting on Red Cell and Iron Metabolism Defects. ACTIVATE: An ongoing, phase 3, randomized, double-blind, placebo-controlled study with mitapivat (AG-348) in adults with pyruvate kinase deficiency who are not regularly transfused. Congress Presentation Poster, Nov. 7, 2019, 1 page.
Grace et al., American Society of Hematology—58th Annual Meeting. Effects of AG-348, a pyruvate kinase activator, on anemia and hemolysis in patients with pyruvate kinase (PK) deficiency: data from the DRIVE PK study. Congress Presentation, Dec. 4, 2016, 14 pages.
Grace et al., American Society of Hematology—58th Annual Meeting. Effects of AG-348, a pyruvate kinase activator, on anemia and hemolysis in patients with pyruvate kinase deficiency: data from the DRIVE PK study. Congress Presentation, Dec. 3, 2016, 1 page. (abstract only).
Grace et al., American Society of Hematology—59th Annual Meeting. Effects of AG-348, a pyruvate kinase activator, in patients with pyruvate kinase deficiency: Updated results from the DRIVE PK study. Congress Presentation Poster, Dec. 10, 2017, 1 page.
Grace et al., American Society of Hematology—59th Annual Meeting. Results update from the DRIVE PK study: Effects of AG-348, a pyruvate kinase activator, in patients with pyruvate kinase deficiency. Congress Presentation, Dec. 9, 2017, 2 pages. (abstract only).
Grace et al., American Society of Hematology—61st Annual Meeting. Long-term safety and efficacy of mitapivat (AG-348), a pyruvate kinase activator, in patients with pyruvate kinase deficiency: The DRIVE PK study. Congress Presentation Poster, Dec. 9, 2019, 1 page.
Grace et al., American Society of Hematology—61st Annual Meeting. Long-term safety and efficacy of mitapivat (AG-348), a pyruvate kinase activator, in patients with pyruvate kinase deficiency: The DRIVE PK study. Congress Presentation, Dec. 3, 2019, 5 pages. (abstract only).
Grace et al., British Blood Transfusion Society—Red Cell Special Interest Group Meeting in 2017. Effects of AG-348, a first in class pyruvate kinase activator, in patients with pyruvate kinase deficiency: Updated results from the DRIVE PK study. Congress Presentation, Sep. 13, 2017, 19 pages.
Grace et al., European Hematology Association—21st Congress. Effects of AG-348, a pyruvate kinase activator, on anemia and hemolysis in patients with pyruvate kinase deficiency. Congress Presentation, Jun. 9, 2016, 1 page. (abstract only).
Grace et al., European Hematology Association—21st Congress. Effects of AG-348, a pyruvate kinase activator, on anemia and hemolysis in patients with pyruvate kinase deficiency: early data from the DRIVE-PK study. Congress Presentation, Jun. 11, 2016, 17 pages.
Grace et al., European Hematology Association—22nd Congress. Effects of AG-348, a pyruvate kinase activator, in patients with pyruvate kinase deficiency: updated results from the DRIVE PK study. Congress Presentation, Jun. 22, 2017, 1 page. (abstract only).
Grace et al., European Hematology Association—22nd Congress. Effects of AG-348, a pyruvate kinase activator, in patients with pyruvate kinase deficiency: updated results from the DRIVE PK study. Congress Presentation, Jun. 22, 2017, 17 pages.
Grace et al., European Hematology Association—25th Congress. Mitapivat (AG-348) long-term safety and efficacy in pyruvate kinase deficiency: 3-year results of the DRIVE PK study. Congress Presentation Poster, Jun. 12, 2020, 1 page.
Grace et al., European Hematology Association—25th Congress. Mitapivat (AG-348) long-term safety and efficacy in pyruvate kinase deficiency: 3-year results of the DRIVE PK study. Congress Presentation, Jun. 11, 2020, 1 page. (abstract only).
Grace et al., Safety and efficacy of mitapivat in pyruvate kinase deficiency. N Eng J Med. Sep. 5, 2019;381(10):933-44.
Grace, American Society of Pediatric Hematology/Oncology—32nd Annual Meeting. Clinical research progress in pyruvate kinase deficiency. Congress Presentation, May 1, 2019, 22 pages.
Grace, Boston Children's Hospital—2016 Grand Rounds. Clinical research progress in a rare anemia: New developments in pyruvate kinase deficiency. Congress Presentation, Apr. 5, 2016, 48 pages.
Grace, Brigham & Women's Hematology—2017 Grand Rounds. Clinical research progress in a rare anemia: New developments in pyruvate kinase deficiency. Congress Presentation, Apr. 25, 2017, 50 pages.
Gross, Gordon Research Conference—Enzymes, Coenzymes and Metabolic Pathways 2017. Treatment of rare genetic diseases by small molecule allosteric activators. Congress Presentation, Jul. 19, 2017, 45 pages.
Gross, University of Massachusetts Amherst Graduate School—Presentation in 2018. Treatment of rare genetic diseases by small molecule allosteric activators. Congress Presentation, Apr. 19, 2018, 49 pages.
Hancock et al., Characteristics and significance of the amorphous state in pharmaceutical systems. J Pharma Sci. Jan. 1997;86(1):1-12.
Harwood et al., Organic Reactions/Purification. Experimental Organic Chemistry, Principles and Practice. Blackwell Science. pp. 127-132, Jan. 1989.
Jia et al., American Society for Clinical Pharmacology and Therapeutics—119th Annual Meeting. Population pharmacokinetics of AG-348 in healthy volunteers and adult patients with pyruvate kinase deficiency. Congress Presentation Poster, Mar. 21, 2018, 1 page.
Jia et al., American Society for Clinical Pharmacology and Therapeutics—119th Annual Meeting. Population pharmacokinetics of AG-348 in healthy volunteers and adult patients with pyruvate kinase deficiency. Congress Presentation, Mar. 21, 2018, 1 page. (abstract only).
Jones et al., Rare Diseases and Orphan Products Breakthrough Summit 2018. Clinical development of a novel oral activator of red cell pyruvate kinase for the treatment of pyruvate kinase deficiency. Congress Presentation Poster, Oct. 15, 2018, 1 page.
Jones et al., Rare Diseases and Orphan Products Breakthrough Summit 2018. Clinical development of a novel oral activator of red cell pyruvate kinase for the treatment of pyruvate kinase deficiency. Congress Presentation, Oct. 15, 2018, 2 pages. (abstract only).
Jouvin et al., European Hematology Association—23rd Congress. Activate-T: A phase 3, open-label study to evaluate the efficacy and safety of AG-348 in regularly transfused adults with pyruvate kinase deficiency. Congress Presentation Poster, Jun. 15, 2018, 1 page.
Jouvin et al., European Hematology Association—23rd Congress. Activate-T: A phase 3, open-label study to evaluate the efficacy and safety of AG-348 in regularly transfused adults with pyruvate kinase deficiency. Congress Presentation, Jun. 14, 2018, 1 page. (abstract only).
Jouvin et al., European Hematology Association—23rd Congress. Activate: A phase 3, randomized, multicenter, double-blind, placebo-controlled study of AG-348 in adults with pyruvate kinase deficiency who are not regularly transfused. Congress Presentation Poster, Jun. 15, 2018, 1 page.
Jouvin et al., European Hematology Association—23rd Congress. Activate: A phase 3, randomized, multicenter, double-blind, placebo-controlled study of AG-348 in adults with pyruvate kinase deficiency who are not regularly transfused. Congress Presentation, Jun. 14, 2018, 2 pages. (abstract only).
Kanno et al., Japanese Society of Hematology—79th Annual Meeting. AG-348, a pyruvate kinase activator, for pyruvate kinase deficiency: Results from the DRIVE PK study. Congress Presentation, Oct. 20, 2017, 2 pages. (abstract only).
Kanno et al., Japanese Society of Hematology—79th Annual Meeting. AG-348, a pyruvate kinase activator, for pyruvate kinase deficiency: Results from the DRIVE PK study. Congress Presentation, Oct. 22, 2017, 15 pages.

(56) References Cited

OTHER PUBLICATIONS

Kung et al., AG-348 enhances pyruvate kinase activity in red blood cells from patients with pyruvate kinase deficiency. Blood. Sep. 14, 2017;130(11):1347-56.
Kung et al., American Society of Hematology—56th Annual Meeting. AG-348 activation of pyruvate kinase in vivo enhances red cell glycolysis in mice. Congress Presentation, Dec. 6, 2014, 2 pages. (abstract only).
Kung et al., American Society of Hematology—60th Annual Meeting. Genotype-response correlation in DRIVE PK, a phase 2 study of AG-348 in patients with pyruvate kinase deficiency. Congress Presentation Poster, Dec. 3, 2018, 1 page.
Kung et al., American Society of Hematology—60th Annual Meeting. Genotype-response correlation in DRIVE PK, a phase 2 study of AG-348 in patients with pyruvate kinase deficiency. Congress Presentation, Dec. 1, 2018, 2 pages. (abstract only).
Kung et al., European Hematology Association—24th Congress. Genotype-response correlation in DRIVE PK, a phase 2 study of mitapivat (AG-348) in patients with pyruvate kinase deficiency. Congress Presentation Poster, Jun. 14, 2019, 1 page.
Kung et al., European Hematology Association—24th Congress. Genotype-response correlation in DRIVE PK, a phase 2 study of mitapivat (AG-348) in patients with pyruvate kinase deficiency. Congress Presentation, Jun. 13, 2019, 2 pages. (abstract only).
Kung, Gordon Research Conference—Red Cells. Mechanism of action of the pyruvate kinase activator mitapivat (AG-348) in hematological disease. Congress Presentation, Jul. 17, 2019, 32 pages.
Kuo et al., American Society of Hematology—61st Annual Meeting. Mitapivat (AG-348), an oral PK-R activator, in adults with non-transfusion dependent thalassemia: a phase 2, open-label, multicenter study in progress. Congress Presentation, Dec. 3, 2019, 2 pages. (abstract only).
Kuo et al., American Society of Hematology—61st Annual Meeting. Mitapivat (AG-348), an oral PK-R activator, in adults with non-transfusion-dependent thalassemia: a phase 2, open-label, multicenter study in progress. Congress Presentation Poster, Dec. 8, 2019, 1 page.
Kuo et al., European Hematology Association—25th Congress. Proof of concept for the oral pyruvate kinase activator mitapivat in adults with non-transfusion-dependent thalassemia: Interim results from an ongoing, phase 2, open-label, multicenter study. Congress Presentation, Jun. 11, 2020, 2 pages. (abstract only).
Kuo et al., European Hematology Association—25th Congress. Proof of concept for the oral pyruvate kinase activator mitapivat in adults with non-transfusion-dependent thalassemia: Interim results from an ongoing, phase 2, open-label, multicenter study. Congress Presentation, Jun. 13, 2020, 14 pages.
Kuo et al., European Hematology Association—25th Congress. Summary of Proof of concept for the oral pyruvate kinase activator mitapivat in adults with non-transfusion-dependent thalassemia: Interim results from an ongoing, phase 2, open-label, multicenter study. Congress Presentation, Jun. 17, 2020, 1 page.
Kuo et al., European Hematology Association Scientific Working Group—2019 Scientific Meeting on Red Cell and Iron Metabolism Defects. An ongoing, open-label, multicenter study with the oral pyruvate kinase activator mitapivat (AG-348) in adults with non-transfusion-dependent thalassemia. Congress Presentation, Nov. 7, 2019, 2 pages. (abstract only).
Kuo et al., European Hematology Association Scientific Working Group—2019 Scientific Meeting on Red Cell and Iron Metabolism Defects. An ongoing, open-label, multicenter study with the oral pyruvate kinase activator mitapivat (AG-348) in adults with non-transfusion-dependent thalassemia. Congress Presentation, Nov. 8, 2019, 11 pages.
Layton et al., British Blood Transfusion Society—2018 Annual Conference. Results update from the DRIVE PK study: Effects of AG-348, a pyruvate kinase activator, in patients with pyruvate kinase deficiency. Congress Presentation Poster, Oct. 4, 2018, 1 page.
Layton et al., British Blood Transfusion Society—2018 Annual Conference. Results update from the DRIVE PK study: Effects of AG-348, a pyruvate kinase activator, in patients with pyruvate kinase deficiency. Congress Presentation, Oct. 4, 2018, 3 pages. (abstract only).
Layton, European Hematology Association Scientific Working Group—2017 Scientific Meeting on Anemias. New drugs for enzymatic defects. Congress Presentation, Feb. 4, 2017, 23 pages.
Le et al., American Society of Hematology—57th Annual Meeting. Population pharmacokinetics and pharmacodynamics of AG-348 in healthy human volunteers guide dose selection for the treatment of pyruvate kinase deficiency. Congress Presentation Poster, Dec. 5, 2015, 1 page.
Le et al., American Society of Hematology—57th Annual Meeting. Population pharmacokinetics and pharmacodynamics of AG-348 in healthy human volunteers guide dose selection for the treatment of pyruvate kinase deficiency. Congress Presentation, Dec. 5, 2015, 2 pages. (abstract only).
Lynch et al., American Society of Hematology—61st Annual Meeting. Mitapivat (AG-348) in adults with pyruvate kinase deficiency who are regularly transfused: a phase 3, open-label, multicenter study (ACTIVATE-T) in progress. Congress Presentation Poster, Dec. 9, 2019, 1 page.
Lynch et al., American Society of Hematology—61st Annual Meeting. Mitapivat (AG-348) in adults with pyruvate kinase deficiency who are regularly transfused: a phase 3, open-label, multicenter, study (ACTIVATE-T) in progress. Congress Presentation, Dec. 3, 2019, 2 pages. (abstract only).
Matte et al., European Hematology Association—21st Congress. The pyruvate kinase activator AG-348 improves murine beta-thalassemic anemia and corrects ineffective erythropoiesis. Congress Presentation, Jun. 10, 2016, 17 pages.
Matte et al., European Hematology Association—21st Congress. The pyruvate kinase activator AG-348 improves murine beta-thalassemic anemia and corrects ineffective erythropoiesis. Congress Presentation, Jun. 9, 2016, 2 pages. (abstract only).
Pladson et al., Gordon Research Conference—Red Cells. Clinical development of a novel oral activator of red cell pyruvate kinase for the treatment of pyruvate kinase deficiency. Congress Presentation Poster, Jul. 17, 2019, 1 page.
Pladson et al., Gordon Research Conference—Red Cells. Clinical development of a novel oral activator of red cell pyruvate kinase for the treatment of pyruvate kinase deficiency. Congress Presentation, Jul. 17, 2019, 2 pages. (abstract only).
Rab et al., AG-348 (Mitapivat), an allosteric activator of red blood cell pyruvate kinase, increases enzymatic activity, protein stability, and ATP levels over a broad range of PKLR genotypes. Haematologica. 2021;106(1):238-49.
Rab et al., American Society of Hematology—61st Annual Meeting. Decreased activity and stability of pyruvate kinase in hereditary hemolytic anemia: a potential target for therapy by AG-348 (mitapivat), an allosteric activator of red blood cell pyruvate kinase. Congress Presentation Poster, Dec. 7, 2019, 1 page.
Rab et al., American Society of Hematology—61st Annual Meeting. Decreased activity and stability of pyruvate kinase in hereditary hemolytic anemia: a potential target for therapy by AG-348 (mitapivat), an allosteric activator of red blood cell pyruvate kinase. Congress Presentation, Dec. 3, 2019, 3 pages. (abstract only).
Rab et al., European Hematology Association—24th Congress. Decreased activity and stability of pyruvake kinase in sickle cell disease and thalassemia: A potential target for therapy. Congress Presentation Poster, Jun. 15, 2019, 1 page.
Rab et al., European Hematology Association—24th Congress. Decreased activity and stability of pyruvake kinase in sickle cell disease and thalassemia: A potential target for therapy. Congress Presentation, Jun. 13, 2019, 2 pages. (abstract only).
Rose et al., Club du Globule Rouge et du Fer—2017 Annual Meeting. Allosteric activator of pyruvate kinase first results: DRIVE PK study Congress Presentation, Sep. 28, 2017, 46 pages.
Rose et al., Societe Francaise d'Hematologie—2017 Annual Congress. Efficacité d'un activateur de la pyruvate kinase (AG-348) sur l'anémie et les paramètres d'hémolyse au cours du déficit en

(56) References Cited

OTHER PUBLICATIONS pyruvate kinase : résultats de l'étude DRIVE PK. Congress Presentation, Mar. 15, 2017, 2 pages, (abstract only).
Rose et al., Societe Francaise d'Hematologie—2017 Annual Congress. Efficacité d'un activateur de la pyruvate kinase (AG-348) sur l'anémie et les parametres d'hémolyse au cours du déficit en pyruvate kinase : résultats de l'étude DRIVE PK. Congress Presentation, Mar. 15, 2017, 32 pages.
Stahl et al., Pharmaceutical salts: properties, selection, and use. Handbook of Pharmaceutical Salts. Jan. 2002;212-14,254,305-6.
STN Accession No. 2014:8. A16A Other Alimentary Tract and Metabolism Products; B3X Other Anti-anaemic Products. 5 pages, Feb. 21, 2020.
Uhlig et al., European Hematology Association—24th Congress. Design of a phase 2, open-label, multicenter study of mitapivat (AG-348) in adults with non-transfusion-dependent thalassemia. Congress Presentation, Jun. 13, 2019, 1 page, (abstract only).
Van Beers et al., American Society of Hematology—61st Annual Meeting. Mitapivat (AG-348) in adults with pyruvate kinase deficiency who are not regularly transfused: a phase 3, randomized, multicenter, double-blind, placebo-controlled study (ACTIVATE) in progress. Congress Presentation, Dec. 3, 2019, 3 pages. (abstract only).
Van Beers et al., European Hematology Association Scientific Working Group—2019 Scientific Meeting on Red Cell and Iron Metabolism Defects. ACTIVATE: an ongoing phase 3 randomised, double-blind, placebo-controlled study with mitapivat (AG-348) in adults with pyruvate kinase deficiency who are not regularly transfused. Congress Presentation, Nov. 7, 2019, 2 pages. (abstract only).
Van Oirschot et al., European Hematology Association—22nd Congress. Ex vivo treatment of red blood cells from 15 pyruvate kinase (PK)-deficient patients with AG-348, an allosteric activator of PK-R, increases ezymatic activity, protein stability and ATP levels. Congress Presentation Poster, Jun. 22, 2017, 1 page.
Van Oirschot et al., European Hematology Association—22nd Congress. Ex vivo treatment of red blood cells from 15 pyruvate kinase (PK)-deficient patients with AG-348, an allosteric activator of PK-R, increases ezymatic activity, protein stability and ATP levels. Congress Presentation, Jun. 22, 2017, 2 pages, (abstract only).
Yang et al., American Society of Hematology—56th Annual Meeting. Phase 1 single (SAD) and multiple (MAD) ascending dose studies of the safety, tolerability, and pharmacokinetics/pharmacodynamics (PK/PD) of AG-348, a first-in-class allosteric activator of pyruvate kinase-R, in healthy subjects. Congress Presentation Poster, Dec. 6, 2014, 1 page.
Yang et al., ENERCA (2015) 6th European Symposium on Rare Anaemias. Phase 1 multiple ascending dose study of the safety, tolerability and pharmacokinetics/pharmacodynamics of AG-348, a first-in-class allosteric activator pf pyruvate kinase R, in healthy subjects. Congress Presentation, Nov. 21, 2015, 22 pages.
Yang et al., ESH/ENERCA Training Course on Diagnosis and Management of Very Rare Red Cell and Iron Disorders. New treatments of pyruvate kinase deficiency: A Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jan. 29, 2016, 2 pages. (abstract only).
Yang et al., European Hematology Association—20th Congress. Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jun. 12, 2015, 19 pages.
Yang et al., European Hematology Association—20th Congress. Phase 1 multiple ascending dose study of the safety, tolerability, and pharmacokinetics/pharmacodynamics of AG-348, a first-in-class allosteric activator of pyruvate kinase-R, in healthy subjects. Congress Presentation, Jun. 13, 2015, 2 pages. (abstract only).
Yang et al., International Drug Discovery Science and Technology—17th Annual Congress. Phase 1 single- and multiple-ascending-dose randomized studies of the safety, pharmacokinetics, and pharmacodynamics of mitapivat (AG-348), a first-in-class allosteric activator of pyruvate kinase R, in healthy volunteers. Congress Presentation, Jul. 25, 2019, 1 page. (abstract only).
Yang et al., International Drug Discovery Science and Technology—17th Annual Congress. Phase 1 single- and multiple-ascending-dose randomized studies of the safety, pharmacokinetics, and pharmacodynamics of mitapivat (AG-348), a first-in-class allosteric activator of pyruvate kinase R, in healthy volunteers. Congress Presentation, Jul. 26, 2019, 19 pages.
Yang et al., Phase 1 single- and multiple-ascending dose randomized studies of the safety, pharmacokinetics, and pharmacodynamics of AG-348, a first-in-class allosteric activator of pyruvate kinase R, in healthy volunteers. Clin Pharmacol Drug Dev. Aug. 9, 2018;8:246-59.
International Search Report and Written Opinion for Application No. PCT/US2018/062197, dated Feb. 20, 2019, 24 pages.
U.S. Appl. No. 16/765,456, filed May 19, 2020, 2020-0277279, Published.

\* cited by examiner

MITAPIVAT THERAPY AND MODULATORS OF CYTOCHROME P450

RELATED APPLICATIONS

This application claims the benefit of U.S. Provisional Application Ser. No. 62/861,600, filed Jun. 14, 2019, the entire teachings of which are incorporated herein by reference.

BACKGROUND

Pyruvate kinase deficiency (PKD) is a disease of the red blood cells caused by a deficiency of the pyruvate kinase R (PKR) enzyme due to recessive mutations of PKLR gene. PKR activators can be beneficial to treat PKD, thalassemia (e.g., beta-thalassemia), abetalipoproteinemia or Bassen-Kornzweig syndrome, sickle cell disease, paroxysmal nocturnal hemoglobinuria, anemia (e.g., congenital anemias (e.g., enzymopathies), hemolytic anemia (e.g., hereditary and/or congenital hemolytic anemia, acquired hemolytic anemia, chronic hemolytic anemia caused by phosphoglycerate kinase deficiency, anemia of chronic diseases, non-spherocytic hemolytic anemia or hereditary spherocytosis). Treatment of PKD is supportive, including blood transfusions, splenectomy, chelation therapy to address iron overload, and/or interventions for other disease-related morbidity. Currently, however, there is no approved medicine that treats the underlying cause of PKD, and thus the etiology of life-long hemolytic anemia.

Mitapivat, also known as AG-348 or by its chemical name N-(4-(4-(cyclopropylmethyl)piperazine-1-carbonyl)phenyl)quinoline-8-sulfonamide, and is represented by the following structural formula:

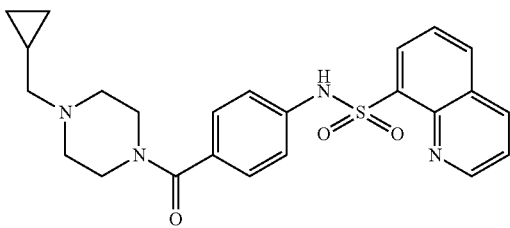 [SMILES: O=C(c1ccc(NS(=O)(=O)c2cccc3cccnc23)cc1)N1CCN(CC2CC2)CC1]

is an allosteric activator of pyruvate kinase R (PKR). See e.g., International Patent Application Publication Nos. WO 2011/002817 and WO 2016/201227.

Mitapivat sulfate is represented by the following structural formula:

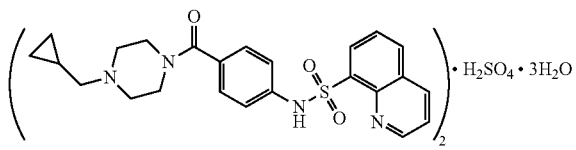

and is currently in Phase 2 and Phase 3 clinical trials as a disease-altering therapy in patients with PKD, hemolytic anemia and thalassemia. See, e.g., U.S. Clinical Trials Identifier Nos. NCT03692052, NCT03559699, NCT03548220, NCT03853798, and NCT02476916.

SUMMARY

Non-clinical studies described in Example 1 show that the PKR activator, mitapivat, is primarily metabolized by the cytochrome P450 3A4 (CYP3A4) or 3A5 (CYP3A5) enzymes (i.e., >90%), with minor contributions from other detoxification enzymes, namely CYP2C8, CYP2C9, and CYP1A2. It has also been found that in a clinical trial, total exposure of mitapivat increased in the presence of itraconazole, a strong CYP3A4A and p-gp inhibitor, compared with dosing of mitapivat sulfate alone. It has further been found that total exposure of mitapivat decreased in the presence of rifampin, a strong CYP3A4A and p-gp inducer, compared with dosing of mitapivat sulfate alone.

Accordingly, the present disclosure provides methods of treating a disease, disorder or a condition with mitapivat or a pharmaceutically acceptable salt thereof and a CYP3A4/5 inducer or a CYP3A4/5 inhibitor. In another aspect, the present disclosure provides methods of treating a disease, disorder or a condition with mitapivat or a pharmaceutically acceptable salt thereof and a p-glycoprotein (p-gp) inhibitor. As used herein, "CYP3A4/5" means cytochrome P450 3A4 (CYP3A4) or 3A5 (CYP3A5). In some embodiments, the pharmaceutically acceptable salt is mitapivat sulfate.

Specifically, in one embodiment, the present disclosure relates to a method of treating pyruvate kinase deficiency (PKD) in a subject, comprising administering to the subject an effective amount of mitapivat or a pharmaceutically acceptable salt thereof and an effective amount of an inhibitor of cytochrome P450 3A4/5 (CYP3A4/5) . In another embodiment, the present disclosure relates to a method of treating sickle cell disease in a subject, comprising administering to the subject an effective amount of mitapivat or a pharmaceutically acceptable salt thereof and an effective amount of an inhibitor of cytochrome P450 3A4/5 (CYP3A4/5). In another embodiment, the present disclosure relates to a method of treating thalassemia (e.g., alpha-thalassemia and beta-thalassemia) in a subject, comprising administering to the subject an effective amount of mitapivat or a pharmaceutically acceptable salt thereof and an effective amount of an inhibitor of cytochrome P450 3A4/5 (CYP3A4/5). In another embodiment, the present disclosure relates to a method of treating hemolytic anemia in a subject, comprising administering to the subject an effective amount of mitapivat or a pharmaceutically acceptable salt thereof and an effective amount of an inhibitor of cytochrome P450 3A4/5 (CYP3A4/5). In some embodiments, the inhibitor of CYP3A4/5 is a moderate CYP3A4/5 inhibitor. In some embodiments, the inhibitor of CYP3A4/5 is a mild CYP3A4/5 inhibitor.

In another embodiment, the present disclosure relates to a method of treating pyruvate kinase deficiency (PKD) in a subject, comprising administering to the subject an effective amount of mitapivat or a pharmaceutically acceptable salt thereof and an effective amount of an inducer of cytochrome P450 3A4/5 (CYP3A4/5) . In another embodiment, the present disclosure relates to a method of treating sickle cell disease in a subject, comprising administering to the subject an effective amount of mitapivat or a pharmaceutically acceptable salt thereof and an effective amount of an inducer of cytochrome P450 3A4/5 (CYP3A4/5). In another embodiment, the present disclosure relates to a method of treating thalassemia (e.g., alpha-thalassemia and/or beta-thalassemia) in a subject, comprising administering to the subject an effective amount of mitapivat or a pharmaceutically acceptable salt thereof and an effective amount of an inducer of cytochrome P450 3A4/5 (CYP3A4/5). In another embodiment, the present disclosure relates to a method of treating hemolytic anemia in a subject, comprising administering to the subject an effective amount of mitapivat or a pharmaceutically acceptable salt thereof and an effective amount of an inducer of cytochrome P450 3A4/5 (CYP3A4/5). In some embodiments, the inducer of CYP3A4/5 is a moderate CYP3A4/5 inducer. In some embodiments, the inhibitor of CYP3A4/5 is a mild CYP3A4/5 inducer.

Specifically, in one embodiment, the present disclosure relates to a method of treating pyruvate kinase deficiency (PKD) in a subject, comprising administering to the subject an effective amount of mitapivat or a pharmaceutically acceptable salt thereof and an effective amount of a p-glycoprotein inhibitor. In another embodiment, the present disclosure relates to a method of treating sickle cell disease in a subject, comprising administering to the subject an effective amount of mitapivat or a pharmaceutically acceptable salt thereof and an effective amount of a p-glycoprotein inhibitor. In another embodiment, the present disclosure relates to a method of treating thalassemia (e.g., alpha-thalassemia and beta-thalassemia) in a subject, comprising administering to the subject an effective amount of mitapivat or a pharmaceutically acceptable salt thereof and an effective amount of a p-glycoprotein inhibitor. In another embodiment, the present disclosure relates to a method of treating hemolytic anemia in a subject, comprising administering to the subject an effective amount of mitapivat or a pharmaceutically acceptable salt thereof and an effective amount of a p-glycoprotein inhibitor. In some embodiments, the p-glycoprotein inhibitor is a moderate p-glycoprotein inhibitor. In some embodiments, the p-glycoprotein inhibitor is a mild p-glycoprotein inhibitor.

The present disclosure further provides methods of treating a disease, disorder or a condition with mitapivat or a pharmaceutically acceptable salt thereof in the absence of a CYP3A4/5 inducer or a CYP3A4/5 inhibitor or p-glycoprotein inhibitor.

Specifically, in one embodiment, the present disclosure relates to a method of treating pyruvate kinase deficiency (PKD) in a subject, comprising administering to the subject an effective amount of mitapivat or a pharmaceutically acceptable salt thereof in the absence of an inducer or an inhibitor of cytochrome P450 3A4/5 (CYP3A4/5), respectively. In another embodiment, the present disclosure relates to a method of treating sickle cell disease in a subject, comprising administering to the subject an effective amount of mitapivat or a pharmaceutically acceptable salt thereof in the absence of an inducer or an inhibitor of cytochrome P450 3A4/5 (CYP3A4/5), respectively. In yet another embodiment, the present disclosure relates to a method of treating thalassemia (e.g., alpha-thalassemia and/or beta-thalassemia) in a subject, comprising administering to the subject an effective amount of mitapivat or a pharmaceutically acceptable salt thereof in the absence of an inducer or an inhibitor of cytochrome P450 3A4/5 (CYP3A4/5), respectively. In yet another embodiment, the present disclosure relates to a method of treating hemolytic anemia in a subject, comprising administering to the subject an effective amount of mitapivat or a pharmaceutically acceptable salt thereof in the absence of an inducer or an inhibitor of cytochrome P450 3A4/5 (CYP3A4/5), respectively. In some embodiments, the inducer of CYP3A4/5 is a strong inducer of CYP3A4/5. In some embodiments, the inducer of CYP3A4/5 is a moderate inducer of CYP3A4/5. In some embodiments, the inhibitor of CYP3A4/5 is a strong inhibitor of CYP3A4/5. In some embodiments, the inhibitor of CYP3A4/5 is a moderate inhibitor of CYP3A4/5.

In another embodiment, the present disclosure relates to a method of treating pyruvate kinase deficiency (PKD) in a subject, comprising administering to the subject an effective amount of mitapivat or a pharmaceutically acceptable salt thereof in the absence of a p-glycoprotein inhibitor. In another embodiment, the present disclosure relates to a method of treating sickle cell disease in a subject, comprising administering to the subject an effective amount of mitapivat or a pharmaceutically acceptable salt thereof in the absence of a p-glycoprotein inhibitor. In yet another embodiment, the present disclosure relates to a method of treating thalassemia (e.g., alpha-thalassemia and/or beta-thalassemia) in a subject, comprising administering to the subject an effective amount of mitapivat or a pharmaceutically acceptable salt thereof in the absence of a p-glycoprotein inhibitor. In yet another embodiment, the present disclosure relates to a method of treating hemolytic anemia in a subject, comprising administering to the subject an effective amount of mitapivat or a pharmaceutically acceptable salt thereof in the absence of a p-glycoprotein inhibitor. In some embodiments, the p-glycoprotein inhibitor is a strong p-glycoprotein inhibitor. In some embodiments, the p-glycoprotein inhibitor is a mild p-glycoprotein inhibitor.

DETAILED DESCRIPTION

Definitions

Figure 1:
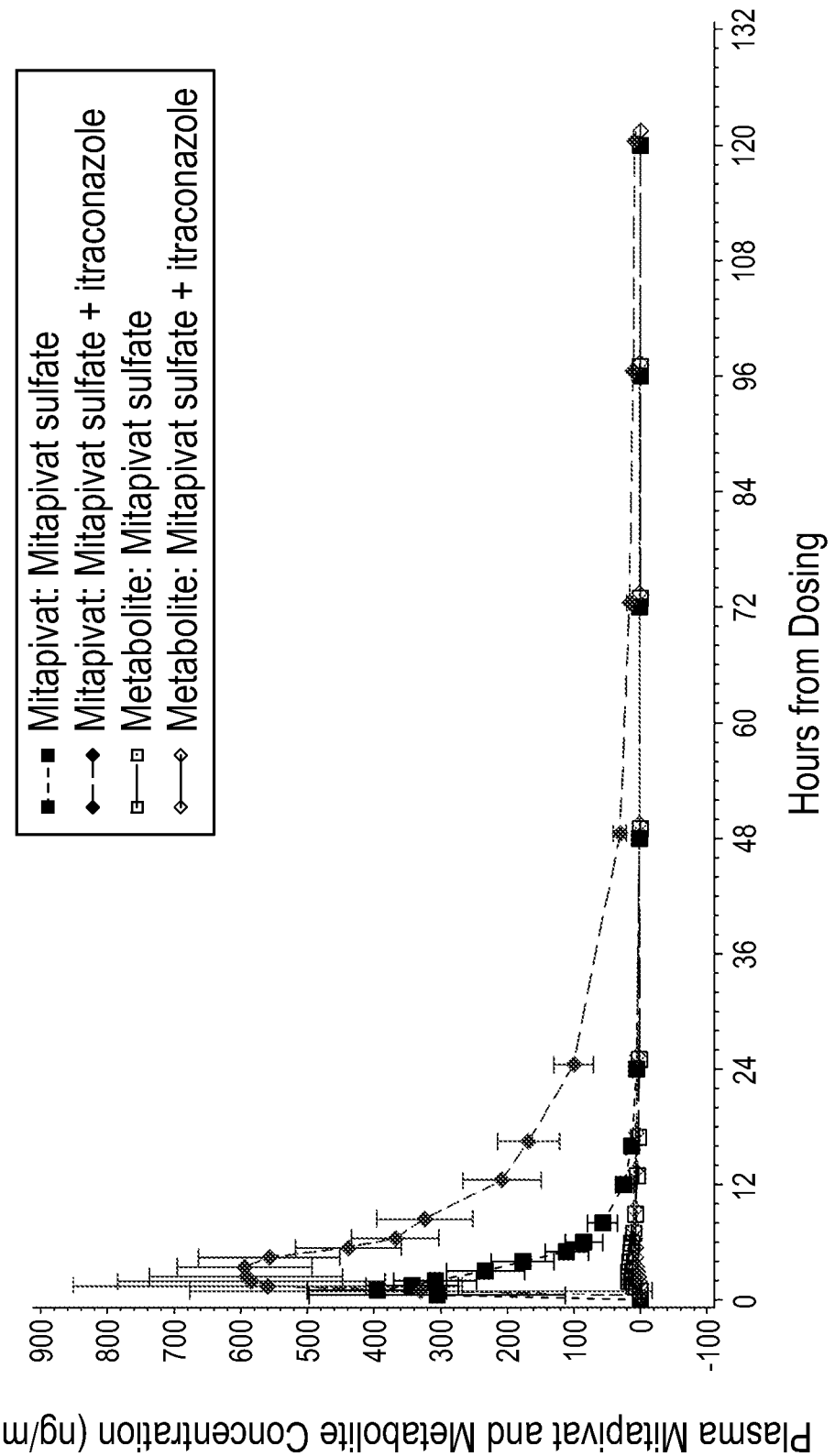
FIG. 1 is a graph showing Arithmetic Mean (SD) Plasma Mitapivat and Metabolite Concentration-Time Profiles following administration of 20 mg mitapivat sulfate alone (Treatment Period 1) and co-administered with multiple doses of 200 mg itraconazole (Treatment Period 2) on linear scale (Part 1). "Metabolite" refers to the CYP3A4 metabolite of mitapivat (see Example 2).

"CYP3A4/5 modulator" refers to any substance, including, but not limited to a small molecule (with a molecular weight of ≤1000 Da, or ≤750 Da, or ≤500 Da), a nucleoside, a nucleotide, a nucleobase, a sugar, a nucleic acid, an amino acid, a polysaccharide, a peptide, a polypeptide, a protein, an antibody, an aptamer, a natural or synthetic plant-based substance, or a complex or a composition comprising any combination of the aforementioned substances, that can modify or alter the activity and/or expression levels of the enzyme cytochrome P450 3A4 (CYP3A4; EC 1.14.13.97) or 3A5 (CYP3A5; EC1.14.14.1). Briefly, the cytochrome P450 (CYP) is a superfamily of detoxification enzymes that are responsible for the oxidative and reductive metabolic transformation of drug medications and the ultimate "clearance", which is the elimination of the drug from the body as determined by the measured plasma levels of the drug and optionally, the drug metabolites, such as the metabolite known to be formed by CYP3A4/5. CYP3A4 and CYP3A5 are two of such enzymes and are largely prevalent in the liver.

A CYP3A4/5 modulator may be a CYP3A4/5 inducer or a CYP3A4/5 inhibitor. A "CYP3A4/5 inducer" or "inducer of CYP3A4/5" is a CYP3A4/5 modulator as defined above that can increase, enhance, stimulate, induce, accelerate or augment the CYP3A4/5 activity from its existing state or native state, such as by at least about 0.1%, 0.2%, 0.5%, 1%, 2%, 3%, 5%, 10%, 15%, 20%, 25%, 30%, 35%, 40%, 45%, 50%, 55%, 60%, 65%, 70%, 75%, 80%, 85%, 90%, 95%, 98%, 99% and 100% or more relative to a reference level, e.g., the level of the CYP3A4/5 activity and/or expression prior to the exposure or contact with the CYP3A4/5 inducer, including all ranges and values therebetween not expressly mentioned above. The CYP3A4/5 inducer activity may cause mitapivat or a pharmaceutically acceptable salt thereof that is co-administered with the CYP3A4/5 inducer to be metabolized and eliminated more quickly from the body, as determined by the measured plasma levels of the compound and its metabolites.

A "CYP3A4/5 inhibitor" or "inhibitor of CYP3A4/5" is a CYP3A4/5 modulator as defined above that can decrease, reduce, inhibit, decelerate, attenuate, or suppress the CYP3A4/5 activity and/or expression from its existing state or native state, such as by at least about 0.1%, 0.2%, 0.5%, 1%, 2%, 3%, 5%, 10%, 15%, 20%, 25%, 30%, 35%, 40%, 45%, 50%, 55%, 60%, 65%, 70%, 75%, 80%, 85%, 90%, 95%, 98%, 99% and 100% or more relative to a reference level, e.g., the level of the CYP3A4/5 activity and/or expression prior to the exposure or contact with the CYP3A4/5 inhibitor, including all ranges and values therebetween not expressly mentioned above. The CYP3A4/5 inhibitor may cause mitapivat or a pharmaceutically acceptable salt thereof that is co-administered with the CYP3A4/5 inhibitor to be metabolized and eliminated more slowly from the body, as determined by the measured plasma levels of the compound and its metabolites.

If an investigational drug is a CYP inducer, it can be classified as a strong, moderate, or mild inducer based on its effect on an index CYP substrate. The convention is to categorize CYP induction in the following ways:

A strong inducer decreases the AUC of a sensitive index CYP by ≥80 percent.

A moderate inducer decreases the AUC of a sensitive index CYP substrate by ≥50 to <80 percent.

A mild inducer decreases the AUC of a sensitive index CYP substrate by ≥20 to <50 percent.

A CYP inhibitor can be classified as a strong, moderate, or mild inhibitor based on its effect on an index CYP substrate. A strong inhibitor increases the AUC of a sensitive index CYP substrate ≥5-fold. A moderate inhibitor increases the AUC of a sensitive index CYP substrate by ≥2- to <5-fold. A mild inhibitor increases the AUC of a sensitive index CYP substrate by ≥1.25- to <2-fold.

A p-glycoprotein inhibitor refers to any substance, including, but not limited to a small molecule (with a molecular weight of ≤1000 Da, or ≤750 Da, or ≤500 Da), a nucleoside, a nucleotide, a nucleobase, a sugar, a nucleic acid, an amino acid, a polysaccharide, a peptide, a polypeptide, a protein, an antibody, an aptamer, a natural or synthetic plant-based substance, or a complex or a composition comprising any combination of the aforementioned substances, that can decrease, reduce, inhibit, decelerate, attenuate, or suppress the p-glycoprotein activity and/or expression from its existing state or native state, such as by at least about 0.1%, 0.2%, 0.5%, 1%, 2%, 3%, 5%, 10%, 15%, 20%, 25%, 30%, 35%, 40%, 45%, 50%, 55%, 60%, 65%, 70%, 75%, 80%, 85%, 90%, 95%, 98%, 99% and 100% or more relative to a reference level, e.g., the level of the p-glycoprotein. In some embodiments, the p-glycoprotein inhibitor is a strong p-glycoprotein inhibitor, selected from the group consisting of amiodarone, azithromycin, captopril, carvedilol, clarithromycin, conivaptan, cyclosporine, diltiazem, dronedarone, erythromycin, felodipine, itraconazole, ketoconazole, lopinavir, ritonavir, quercetin, quinidine, ranolazine ticagrelor, and erapamil.

The terms "effective amount" and "therapeutically effective amount" are used interchangeably throughout the present disclosure, whether referring to mitapivat or a pharmaceutically acceptable salt thereof, a CYP3A4/5 inducer, or a CYP3A4/5 inhibitor.

An "effective amount" of mitapivat or a pharmaceutically acceptable thereof is an amount sufficient to provide a therapeutic benefit in the treatment of pyruvate kinase deficiency (PKD), thalassemia (e.g., alfa-thalassemia, beta-thalassemia or non-transfusion-dependent thalassemia), abetalipoproteinemia or Bassen-Kornzweig syndrome, sickle cell disease, paroxysmal nocturnal hemoglobinuria, anemia (e.g., congenital anemias (e.g., enzymopathies), hemolytic anemia (e.g., hereditary and/or congenital hemolytic anemia, acquired hemolytic anemia, chronic hemolytic anemia, chronic hemolytic anemia caused by phosphoglycerate kinase deficiency, anemia of chronic diseases, non-spherocytic hemolytic anemia or hereditary spherocytosis), as well as all other conditions disclosed in the section "Diseases, Disorders and Conditions" in the present disclosure, i.e., conditions that are responsive to treatment with a PKR activator such as mitapivat or a pharmaceutically acceptable salt thereof. Such diseases, disorders and conditions are hereinafter referred as "a PKR activator-responsive condition" when referring to any one of these conditions or "PKR activator-responsive conditions" when referring to these conditions collectively. Additionally or alternatively, an "effective amount" of mitapivat or a pharmaceutically acceptable salt thereof is an amount sufficient to delay or minimize one or more effects or symptoms associated with these conditions. In one aspect, an "effective amount" of mitapivat or a pharmaceutically acceptable salt thereof means an amount of mitapivat or a pharmaceutically acceptable salt thereof, alone or in combination with other therapies, which provides a therapeutic benefit in the treatment of the condition. The term "effective amount" can encompass an amount that improves overall therapy, reduces or avoids effects, symptoms, signs, or causes of the condition, and/or enhances the therapeutic efficacy of another therapeutic agent. In certain embodiments, an "effective amount" of mitapivat or a pharmaceutically acceptable salt thereof is an amount sufficient for eliciting measurable activation of wild-type or mutant PKR. In certain embodiments, an "effective amount" of mitapivat or a pharmaceutically acceptable salt thereof is an amount sufficient for regulating 2,3-diphosphoglycerate levels in blood in need thereof or for treating PKR activator-responsive conditions or treating diseases or conditions that are associated with increased 2,3-diphosphoglycerate levels (e.g., liver diseases). In certain embodiments, an effective amount of mitapivat or a pharmaceutically acceptable salt thereof is an amount sufficient for eliciting measurable activation of wild-type or mutant PKR and for regulating 2,3-diphosphoglycerate levels in blood in need thereof or for treating PKR activator-responsive conditions or treating diseases or conditions that are associated with increased 2,3-diphosphoglycerate levels (e.g., liver diseases). In one aspect, the effective amount is the amount required to generate a subject's hemoglobin response of ≥1.0 g/dL (such as ≥1.5 g/dL or ≥2.0 g/dL) increase in Hb concentration from baseline. In one aspect, the subject's baseline Hb concentration is the average of all available Hb concentrations before treatment with a compound described herein. In certain aspects, the effective amount is the amount required to reduce the patient's transfusion burden. In one aspect, the effective amount of mitapivat or a pharmaceutically acceptable salt thereof (e.g., mitapivat sulfate) is between about 0.01-100 mg/kg body weight/day of mitapivat or a pharmaceutically acceptable salt thereof (e.g., mitapivat sulfate), e.g., about 0.1-100 mg/kg body weight/day.

Concomitant medications will be commonly used with mitapivat or a pharmaceutically acceptable salt thereof (e.g., mitapivat sulfate). An "effective amount" of the drug (e.g., an effective amount of a CYP3A4/5 inducer or an effective amount of a CYP3A4/5 inhibitor) being co-administered with mitapivat or a pharmaceutically acceptable salt thereof (e.g., mitapivat sulfate) is an amount sufficient to provide a desired therapeutic benefit. Drugs that are being co-administered with mitapivat or a pharmaceutically acceptable salt thereof (e.g., mitapivat sulfate), including some of the current antiarrhythmics, antibiotics, antidepressants, antifungals, calcium channel blockers, $H_2$ receptor antagonists, non-nucleoside reverse transcriptase inhibitors (NNRTI), protease inhibitors, etc., will sometimes be CYP3A4/5 inducers or CYP3A4/5 inhibitors. In such instances, the amount of mitapivat or a pharmaceutically acceptable salt thereof (e.g., mitapivat sulfate) or the amount of the drug being co-administered should be adjusted to reduce effects of a drug-drug interaction between mitapivat or a pharmaceutically acceptable salt thereof (e.g., mitapivat sulfate) and the co-administered drug.

In one aspect, an effective amount of a CYP3A4/5 inducer is between about 0.1-1000 mg/kg/day of a CYP3A4/5 inducer, e.g., about 1.0-1000 mg/kg/day, depending on the drug that is co-administered with.

In one aspect, an effective amount of a CYP3A4/5 inhibitor is between about 0.1-1000 mg/kg/day of a CYP3A4/5 inhibitor, e.g., about 1.0-1000 mg/kg/day, depending on the drug that is co-administered with.

In one aspect, an effective amount of a p-gp inhibitor is between about 0.1-1000 mg/kg/day of a p-gp inhibitor, e.g., about 1.0-1000 mg/kg/day, depending on the drug that is co-administered with.

As used herein, reduction in transfusion burden means at least 20% reduction in the number of RBC units transfused within at least 5 weeks of treatment. In certain embodiments, the reduction in transfusion burden is ≥33% reduction in the number of RBC units transfused within at least 5 weeks of treatment. In certain embodiments, reduction of transfusion burden is ≥33% reduction in the number of RBC units transfused within at least 10 weeks (e.g., at least 20 weeks or at least 24 weeks) of treatment.

The term "activating" as used herein means an agent that (measurably) increases the activity of wild type pyruvate kinase R (wt PKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The terms "treatment," "treat," and "treating" refer to reversing, alleviating, reducing the likelihood of developing, or inhibiting the progress of a disease or disorder, or one or more effects or symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to reduce the likelihood of or delay their recurrence.

As used herein the terms "subject" and "patient" may be used interchangeably, and means a mammal in need of treatment with mitapivat or a pharmaceutically acceptable salt thereof (e.g., mitapivat sulfate).

The term "pharmaceutically acceptable salt" when referring to a pharmaceutically acceptable salt of mitapivat, refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art, for example, Berge et al. describe pharmaceutically acceptable salts in detail in J. Pharmaceutical Sciences, 1977, 66, 1-19. Pharmaceutically acceptable salts of mitapivat include those derived from suitable inorganic and organic acids. Examples of pharmaceutically acceptable acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, besylate bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, gentisate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, tosylate p-toluenesulfonate, undecanoate, valerate salts, and the like. Preferably, a pharmaceutically acceptable salt of mitapivat is a sulfate salt.

As used herein, the terms "about" and "approximately" are used herein to mean within the typical ranges of tolerance in the art. In one embodiment, "about" means within 2 standard deviations from the mean value. In one embodiment, "about" means ±10%. In one embodiment, "about" means ±5%. When "about" is present before a series of numbers of number ranges, it is understood that the term can apply to any and each of the numbers and ranges recited in the series.

Compositions and Administration he effective amount of mitapivat, in accordance with a method of the invention, may be administered in the form of a pharmaceutical composition comprising mitapivat or a pharmaceutically acceptable salt thereof (e.g., mitapivat sulfate), together with a pharmaceutically acceptable carrier.

Pharmaceutical compositions of mitapivat or a pharmaceutically acceptable salt thereof (e.g., mitapivat sulfate) can be prepared by any method known in the art of pharmacology. In general, such preparatory methods include the steps of bringing of mitapivat or a pharmaceutically acceptable salt thereof (e.g., mitapivat sulfate) into association with a carrier and/or one or more other accessory ingredients, and then, if necessary and/or desirable, shaping and/or packaging the product into a desired single- or multi-dose unit.

Pharmaceutically acceptable carriers used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Exemplary carriers, diluents, granulating and/or dispersing agents, surface active agents and/or emulsifiers, binding agents, preservatives, antioxidants, chelating agent, antifungal preservatives, alcohol preservatives, acidic preservatives, other types of preservatives, buffering agents, lubricating agents, and natural oils that can be included in a pharmaceutical composition of mitapivat or a pharmaceutically acceptable salt thereof (e.g., mitapivat sulfate) as disclosed in International Patent Application No. WO2019/104134.

Pharmaceutical compositions of mitapivat or a pharmaceutically acceptable salt thereof (e.g., mitapivat sulfate) may be administered orally, parenterally, by inhalation spray, topically, rectally, nasally, buccally, transmucosally, or in an ophthalmic preparation. The term "parenteral" as used herein includes subcutaneous, intravenous, intramuscular, intra-articular, intra-synovial, intrasternal, intrathecal, intrahepatic, intralesional and intracranial injection or infusion techniques. In one aspect, the pharmaceutical compositions provided herewith are orally administered in an orally acceptable dosage form including, but not limited to, capsules, tablets, emulsions and aqueous suspensions, dispersions and solutions. In the case of tablets for oral use, carriers which are commonly used include one or more substances selected from microcrystalline cellulose, mannitol, croscarmellose sodium, and sodium stearyl fumarate. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

A secondary drug can be co-administered with mitapivat or a pharmaceutically acceptable salt thereof (e.g., mitapivat sulfate). The effective amount of a secondary drug that is co-administered with mitapivat or a pharmaceutically acceptable salt thereof (e.g., mitapivat sulfate), such as a CYP3A4/5 inducer or a CYP3A4/5 inhibitor or a p-gp inhibitor, if used in a method of the invention, may also be administered in the form of a pharmaceutical composition comprising the CYP3A4/5 inducer or the CYP3A4/5 inhibitor or the p-gp inhibitor, together with a pharmaceutically acceptable carrier. Pharmaceutical compositions of the secondary drug may be prepared and administered as described above for pharmaceutical compositions of mitapivat or a pharmaceutically acceptable salt thereof (e.g., mitapivat sulfate).

In one aspect, mitapivat or a pharmaceutically acceptable salt thereof (e.g. mitapivat sulfate) is formulated as a tablet composition together with a pharmaceutically acceptable carrier, in accordance with the disclosures of International Patent Application No. WO2019/104134.

In one embodiment, in therapies comprising mitapivat or a pharmaceutically acceptable salt thereof (e.g., mitapivat sulfate) and a secondary drug (e.g., a CYP3A4/5 inducer or a CYP3A4/5 inhibitor), mitapivat or a pharmaceutically acceptable salt thereof (e.g., mitapivat sulfate) and the secondary drug are administered "concurrently" to the subject, which means that the subject is administered both drugs on the same day on all days of the treatment period. In one embodiment, mitapivat or a pharmaceutically acceptable salt thereof (e.g., mitapivat sulfate) and the secondary drug are administered "sequentially" to the subject, which means that the subject is administered either of the two drugs on all days of the treatment period, but not both drugs. In another embodiment, mitapivat or a pharmaceutically acceptable salt thereof (e.g., mitapivat sulfate) and the secondary drug are administered "sequentially and concurrently" to the subject, which means that the subject is administered either of the two drugs on certain days of the treatment period, but not both drugs; and the subject is administered both drugs on the same day on other days of the treatment period.

Doses and Dosing Regimens

The amount of mitapivat or a pharmaceutically acceptable salt thereof (e.g., mitapivat sulfate) that may be combined with carrier materials to produce a composition in a single dosage form will vary depending upon the subject to be treated and the particular mode of administration. For example, a specific dosage and treatment regimen for any particular subject will depend upon a variety of factors, including age, body weight, general health, sex, diet, time of administration, rate of excretion, drug combination, the judgment of the treating physician, and the severity of the particular disease being treated. The amount of mitapivat or a pharmaceutically acceptable salt thereof will also depend upon the particular form (e.g., free base, salt form, crystalline form, etc.) in the composition. In one aspect, a provided composition may be formulated such that a dosage equivalent to about 0.001 to about 100 mg/kg body weight/day of mitapivat or a pharmaceutically acceptable salt thereof (e.g., about 0.5 to about 100 mg/kg of mitapivat or a pharmaceutically acceptable salt thereof) can be administered to a subject receiving these compositions. Alternatively, dosages equivalent to 1 mg/kg and 1000 mg/kg of mitapivat or a pharmaceutically acceptable salt thereof every 4 to 120 hours is also acceptable.

In one aspect, mitapivat or a pharmaceutically acceptable salt thereof is formulated for administration at a dose of equivalent to about 2 mg to about 3000 mg of mitapivat. In certain embodiments, the dose is an oral dose. In certain embodiments, mitapivat or a pharmaceutically acceptable salt thereof is formulated equivalent to about 2 mg to about 3000 mg of mitapivat. In certain embodiments, mitapivat or a pharmaceutically acceptable salt thereof is formulated equivalent to about 5 mg to about 350 mg of mitapivat. In certain embodiments, mitapivat or a pharmaceutically acceptable salt thereof is formulated equivalent to about 5 mg to about 200 mg of mitapivat. In certain embodiments, mitapivat or a pharmaceutically acceptable salt thereof is formulated equivalent to about 5 mg to about 100 mg of mitapivat. In certain embodiments, mitapivat or a pharmaceutically acceptable salt thereof is formulated equivalent to about 5 mg of mitapivat. In certain embodiments, mitapivat or a pharmaceutically acceptable salt thereof is formulated equivalent to about 10 mg of mitapivat. In certain embodiments, mitapivat or a pharmaceutically acceptable salt thereof is formulated equivalent to about 15 mg of mitapivat. In certain embodiments, mitapivat or a pharmaceutically acceptable salt thereof is formulated equivalent to about 20 mg of mitapivat. In certain embodiments, mitapivat or a pharmaceutically acceptable salt thereof is formulated equivalent to about 25 mg of mitapivat. In certain embodiments, mitapivat or a pharmaceutically acceptable salt thereof is formulated equivalent to about 30 mg of mitapivat. In certain embodiments, mitapivat or a pharmaceutically acceptable salt thereof is formulated equivalent to about 35 mg of mitapivat. In certain embodiments, mitapivat or a pharmaceutically acceptable salt thereof is formulated equivalent to about 40 mg of mitapivat. In certain embodiments, mitapivat or a pharmaceutically acceptable salt thereof is formulated equivalent to about 45 mg of mitapivat. In certain embodiments, mitapivat or a pharmaceutically acceptable salt thereof is formulated equivalent to about 50 mg of mitapivat. In certain embodiments, mitapivat or a pharmaceutically acceptable salt thereof is formulated equivalent to about 55 mg of mitapivat. In certain embodiments, mitapivat or a pharmaceutically acceptable salt thereof is formulated equivalent to about 60 mg of mitapivat. In certain embodiments, mitapivat or a pharmaceutically acceptable salt thereof is formulated equivalent to about 65 mg of mitapivat. In certain embodiments, mitapivat or a pharmaceutically acceptable salt thereof is formulated equivalent to about 70 mg of mitapivat. In certain embodiments, mitapivat or a pharmaceutically acceptable salt thereof is formulated equivalent to about 75 mg of mitapivat. In certain embodiments, mitapivat or a pharmaceutically acceptable salt thereof is formulated equivalent to about 80 mg of mitapivat. In certain embodiments, mitapivat or a pharmaceutically acceptable salt thereof is formulated equivalent to about 85 mg of mitapivat. In certain embodiments, mitapivat or a pharmaceutically acceptable salt thereof is formulated equivalent to about 90 mg of mitapivat. In certain embodiments, mitapivat or a pharmaceutically acceptable salt thereof is formulated equivalent to about 95 mg of mitapivat. In certain embodiments, mitapivat or a pharmaceutically acceptable salt thereof is formulated equivalent to about 100 mg of mitapivat. In certain embodiments, mitapivat or a pharmaceutically acceptable salt thereof is formulated equivalent to about 110 mg of mitapivat. In certain embodiments, mitapivat or a pharmaceutically acceptable salt thereof is formulated equivalent to about 120 mg of mitapivat. In certain embodiments, mitapivat or a pharmaceutically acceptable salt thereof is formulated equivalent to about 130 mg of mitapivat. In certain embodiments, mitapivat or a pharmaceutically acceptable salt thereof is formulated equivalent to about 140 mg of mitapivat. In certain embodiments, mitapivat or a pharmaceutically acceptable salt thereof is formulated equivalent to about 150 mg of mitapivat. In certain embodiments, mitapivat or a pharmaceutically acceptable salt thereof is formulated equivalent to about 160 mg of mitapivat. In certain embodiments, mitapivat or a pharmaceutically acceptable salt thereof is formulated equivalent to about 170 mg of mitapivat. In certain embodiments, mitapivat or a pharmaceutically acceptable salt thereof is formulated equivalent to about 180 mg of mitapivat. In certain embodiments, mitapivat or a pharmaceutically acceptable salt thereof is formulated equivalent to about 190 mg of mitapivat. In certain embodiments, mitapivat or a pharmaceutically acceptable salt thereof is formulated equivalent to about 200 mg of mitapivat. In certain embodiments, mitapivat or a pharmaceutically acceptable salt thereof is formulated equivalent to about 210 mg of mitapivat. In certain embodiments, mitapivat or a pharmaceutically acceptable salt thereof is formulated equivalent to about 220 mg of mitapivat. In certain embodiments, mitapivat or a pharmaceutically acceptable salt thereof is formulated equivalent to about 230 mg of mitapivat. In certain embodiments, mitapivat or a pharmaceutically acceptable salt thereof is formulated equivalent to about 240 mg of mitapivat. In certain embodiments, mitapivat or a pharmaceutically acceptable salt thereof is formulated equivalent to about 250 mg of mitapivat. In certain embodiments, mitapivat or a pharmaceutically acceptable salt thereof is formulated equivalent to about 260 mg of mitapivat. In certain embodiments, mitapivat or a pharmaceutically acceptable salt thereof is formulated equivalent to about 270 mg of mitapivat. In certain embodiments, mitapivat or a pharmaceutically acceptable salt thereof is formulated equivalent to about 280 mg of mitapivat. In certain embodiments, mitapivat or a pharmaceutically acceptable salt thereof is formulated equivalent to about 290 mg of mitapivat. In certain embodiments, mitapivat or a pharmaceutically acceptable salt thereof is formulated equivalent to about 300 mg of mitapivat. In certain embodiments, mitapivat or a pharmaceutically acceptable salt thereof is formulated equivalent to about 300 to 360 mg of mitapivat. In certain embodiment, the pharmaceutically acceptable salt of mitapivat is mitapivat sulfate.

In certain embodiments, mitapivat or a pharmaceutically acceptable salt thereof is formulated for administration at a dose equivalent to about 2 mg to about 3000 mg of mitapivat per day. In certain embodiments, mitapivat or a pharmaceutically acceptable salt thereof is formulated for administration at a dose equivalent to about 5 mg to about 500 mg of mitapivat of per day. In certain embodiments, mitapivat or a pharmaceutically acceptable salt thereof is formulated for administration at a dose equivalent to about 5 mg to about 200 mg of mitapivat per day. In certain embodiments, mitapivat or a pharmaceutically acceptable salt thereof is formulated for administration at a dose equivalent to about 5 mg of mitapivat per day. In certain embodiments, mitapivat or a pharmaceutically acceptable salt thereof is formulated for administration at a dose equivalent to about 5 mg to about 10 mg of mitapivat per day. In certain embodiments, mitapivat or a pharmaceutically acceptable salt thereof is formulated for administration at a dose of about 15 mg equivalent to mitapivat per day. In certain embodiments, mitapivat or a pharmaceutically acceptable salt thereof is formulated for administration at a dose equivalent to about 20 mg of mitapivat per day. In certain embodiments, mitapivat or a pharmaceutically acceptable salt thereof is formulated for administration at a dose equivalent to about 25 mg of mitapivat per day. In certain embodiments, mitapivat or a pharmaceutically acceptable salt thereof is formulated for administration at a dose equivalent to about 30 mg of mitapivat per day. In certain embodiments, mitapivat or a pharmaceutically acceptable salt thereof is formulated for administration at a dose equivalent to about 35 mg of mitapivat per day. In certain embodiments, mitapivat or a pharmaceutically acceptable salt thereof is formulated for administration at a dose equivalent to about 40 mg of mitapivat per day. In certain embodiments, mitapivat or a pharmaceutically acceptable salt thereof is formulated for administration at a dose equivalent to about 45 mg of mitapivat per day. In certain embodiments, mitapivat or a pharmaceutically acceptable salt thereof is formulated for administration at a dose equivalent to about 50 mg of mitapivat thereof per day. In certain embodiments, mitapivat or a pharmaceutically acceptable salt thereof is formulated for administration at a dose equivalent to about 55 mg of mitapivat thereof per day. In certain embodiments, mitapivat or a pharmaceutically acceptable salt thereof is formulated for administration at a dose equivalent to about 60 mg of mitapivat per day. In certain embodiments, mitapivat or a pharmaceutically acceptable salt thereof is formulated for administration at a dose equivalent to about 70 mg of mitapivat per day. In certain embodiments, mitapivat or a pharmaceutically acceptable salt thereof is formulated for administration at a dose equivalent to about 80 mg of mitapivat per day. In certain embodiments, mitapivat or a pharmaceutically acceptable salt thereof is formulated for administration at a dose equivalent to about 90 mg of mitapivat per day. In certain embodiments, mitapivat or a pharmaceutically acceptable salt thereof is formulated for administration at a dose equivalent to about 100 mg of mitapivat per day. In certain embodiments, mitapivat or a pharmaceutically acceptable salt thereof is formulated for administration at a dose equivalent to about 110 mg of mitapivat per day. In certain embodiments, mitapivat or a pharmaceutically acceptable salt thereof is formulated for administration at a dose equivalent to about 120 mg of mitapivat per day. In certain embodiments, mitapivat or a pharmaceutically acceptable salt thereof is formulated for administration at a dose equivalent to about 130 mg of mitapivat per day. In certain embodiments, mitapivat or a pharmaceutically acceptable salt thereof is formulated for administration at a dose equivalent to about 140 mg of mitapivat per day. In certain embodiments, mitapivat or a pharmaceutically acceptable salt thereof is formulated for administration at a dose equivalent to about 150 mg of mitapivat per day. In certain embodiments, mitapivat or a pharmaceutically acceptable salt thereof is formulated for administration at a dose equivalent to about 160 mg of mitapivat per day. In certain embodiments, mitapivat or a pharmaceutically acceptable salt thereof is formulated for administration at a dose equivalent to about 170 mg of mitapivat per day. In certain embodiments, mitapivat or a pharmaceutically acceptable salt thereof is formulated for administration at a dose equivalent to about 180 mg of mitapivat per day. In certain embodiments, mitapivat or a pharmaceutically acceptable salt thereof is formulated for administration at a dose equivalent to about 190 mg of mitapivat per day. In certain embodiments, mitapivat or a pharmaceutically acceptable salt thereof is formulated for administration at a dose equivalent to about 200 mg of mitapivat per day. In certain embodiments, mitapivat or a pharmaceutically acceptable salt thereof is formulated for administration at a dose equivalent to about 210 mg of mitapivat per day. In certain embodiments, mitapivat or a pharmaceutically acceptable salt thereof is formulated for administration at a dose equivalent to about 220 mg of mitapivat per day. In certain embodiments, mitapivat or a pharmaceutically acceptable salt thereof is formulated for administration at a dose equivalent to about 230 mg of mitapivat per day. In certain embodiments, mitapivat or a pharmaceutically acceptable salt thereof is formulated for administration at a dose equivalent to about 240 mg of mitapivat per day. In certain embodiments, mitapivat or a pharmaceutically acceptable salt thereof is formulated for administration at a dose equivalent to about 250 mg of mitapivat per day. In certain embodiments, mitapivat or a pharmaceutically acceptable salt thereof is formulated for administration at a dose equivalent to about 260 mg of mitapivat per day. In certain embodiments, mitapivat or a pharmaceutically acceptable salt thereof is formulated for administration at a dose equivalent to about 270 mg of mitapivat per day. In certain embodiments, mitapivat or a pharmaceutically acceptable salt thereof is formulated for administration at a dose equivalent to about 280 mg of mitapivat per day. In certain embodiments, mitapivat or a pharmaceutically acceptable salt thereof is formulated for administration at a dose equivalent to about 290 mg of mitapivat per day. In certain embodiments, mitapivat or a pharmaceutically acceptable salt thereof is formulated for administration at a dose equivalent to about 300 mg of mitapivat per day. In certain embodiments, mitapivat or a pharmaceutically acceptable salt thereof is formulated for administration at a dose equivalent to about 300-360 mg of mitapivat per day. Dosing can be once, twice, or three times daily. In one aspect, mitapivat or a pharmaceutically acceptable salt thereof is formulated for administration at a dose equivalent to about 5 mg of mitapivat thereof twice per day. In one aspect, mitapivat or a pharmaceutically acceptable salt thereof is formulated for administration at a dose equivalent to about 10 mg of mitapivat thereof twice per day. In one aspect, mitapivat or a pharmaceutically acceptable salt thereof is formulated for administration at a dose equivalent to about 15 mg of mitapivat thereof twice per day. In one aspect, mitapivat or a pharmaceutically acceptable salt thereof is formulated for administration at a dose equivalent to about 20 mg of mitapivat twice per day. In one aspect, mitapivat or a pharmaceutically acceptable salt thereof is formulated for administration at a dose equivalent to about 25 mg of mitapivat thereof twice per day. In one aspect, mitapivat or a pharmaceutically acceptable salt thereof is formulated for administration at a dose equivalent to about 30 mg of mitapivat thereof twice per day. In one aspect, mitapivat or a pharmaceutically acceptable salt thereof is formulated for administration at a dose equivalent to about 35 mg of mitapivat thereof twice per day. In one aspect, mitapivat or a pharmaceutically acceptable salt thereof is formulated for administration at a dose equivalent to about 40 mg of mitapivat thereof twice per day. In one aspect, mitapivat or a pharmaceutically acceptable salt thereof is formulated for administration at a dose equivalent to about 45 mg of mitapivat thereof twice per day. In one aspect, mitapivat or a pharmaceutically acceptable salt thereof is formulated for administration at a dose equivalent to about 50 mg of mitapivat twice per day. In one aspect, mitapivat or a pharmaceutically acceptable salt thereof is formulated for administration at a dose equivalent to about 55 mg of mitapivat thereof twice per day. In one aspect, mitapivat or a pharmaceutically acceptable salt thereof is formulated for administration at a dose equivalent to about 60 mg of mitapivat thereof twice per day. In one aspect, mitapivat or a pharmaceutically acceptable salt thereof is formulated for administration at a dose equivalent to about 65 mg of mitapivat thereof twice per day. In one aspect, mitapivat or a pharmaceutically acceptable salt thereof is formulated for administration at a dose equivalent to about 70 mg of mitapivat thereof twice per day. In one aspect, mitapivat or a pharmaceutically acceptable salt thereof is formulated for administration at a dose equivalent to about 75 mg of mitapivat thereof twice per day. In one aspect, mitapivat or a pharmaceutically acceptable salt thereof is formulated for administration at a dose equivalent to about 80 mg of mitapivat thereof twice per day. In one aspect, mitapivat or a pharmaceutically acceptable salt thereof is formulated for administration at a dose equivalent to about 85 mg of mitapivat thereof twice per day. In one aspect, mitapivat or a pharmaceutically acceptable salt thereof is formulated for administration at a dose equivalent to about 90 mg of mitapivat thereof twice per day. In one aspect, mitapivat or a pharmaceutically acceptable salt thereof is formulated for administration at a dose equivalent to about 95 mg of mitapivat thereof twice per day. In one aspect, mitapivat or a pharmaceutically acceptable salt thereof is formulated for administration at a dose equivalent to about 100 mg of mitapivat twice per day. In another aspect, mitapivat or a pharmaceutically acceptable salt thereof is formulated for administration at a dose equivalent to about 5 mg of mitapivat thereof once per day. In another aspect, mitapivat or a pharmaceutically acceptable salt thereof is formulated for administration at a dose equivalent to about 10 mg of mitapivat thereof once per day. In another aspect, mitapivat or a pharmaceutically acceptable salt thereof is formulated for administration at a dose equivalent to about 15 mg of mitapivat thereof once per day. In one aspect, mitapivat or a pharmaceutically acceptable salt thereof is formulated for administration at a dose equivalent to about 20 mg of mitapivat once per day. In another aspect, mitapivat or a pharmaceutically acceptable salt thereof is formulated for administration at a dose equivalent to about 25 mg of mitapivat thereof once per day. In another aspect, mitapivat or a pharmaceutically acceptable salt thereof is formulated for administration at a dose equivalent to about 30 mg of mitapivat thereof once per day. In another aspect, mitapivat or a pharmaceutically acceptable salt thereof is formulated for administration at a dose equivalent to about 35 mg of mitapivat thereof once per day. In another aspect, mitapivat or a pharmaceutically acceptable salt thereof is formulated for administration at a dose equivalent to about 40 mg of mitapivat thereof once per day. In another aspect, mitapivat or a pharmaceutically acceptable salt thereof is formulated for administration at a dose equivalent to about 45 mg of mitapivat thereof once per day. In one aspect, mitapivat or a pharmaceutically acceptable salt thereof is formulated for administration at a dose equivalent to about 50 mg of mitapivat once per day. In another aspect, mitapivat or a pharmaceutically acceptable salt thereof is formulated for administration at a dose equivalent to about 55 mg of mitapivat thereof once per day. In another aspect, mitapivat or a pharmaceutically acceptable salt thereof is formulated for administration at a dose equivalent to about 60 mg of mitapivat thereof once per day. In another aspect, mitapivat or a pharmaceutically acceptable salt thereof is formulated for administration at a dose equivalent to about 65 mg of mitapivat thereof once per day. In another aspect, mitapivat or a pharmaceutically acceptable salt thereof is formulated for administration at a dose equivalent to about 70 mg of mitapivat thereof once per day. In another aspect, mitapivat or a pharmaceutically acceptable salt thereof is formulated for administration at a dose equivalent to about 75 mg of mitapivat thereof once per day. In another aspect, mitapivat or a pharmaceutically acceptable salt thereof is formulated for administration at a dose equivalent to about 80 mg of mitapivat thereof once per day. In another aspect, mitapivat or a pharmaceutically acceptable salt thereof is formulated for administration at a dose equivalent to about 85 mg of mitapivat thereof once per day. In another aspect, mitapivat or a pharmaceutically acceptable salt thereof is formulated for administration at a dose equivalent to about 95 mg of mitapivat thereof once per day. In one aspect, mitapivat or a pharmaceutically acceptable salt thereof is formulated for administration at a dose equivalent to about 100 mg of mitapivat once per day. In another aspect, mitapivat or a pharmaceutically acceptable salt thereof is formulated for administration at a dose equivalent to about 110 mg of mitapivat thereof once per day. In another aspect, mitapivat or a pharmaceutically acceptable salt thereof is formulated for administration at a dose equivalent to about 120 mg of mitapivat thereof once per day. In another aspect, mitapivat or a pharmaceutically acceptable salt thereof is formulated for administration at a dose equivalent to about 130 mg of mitapivat thereof once per day. In another aspect, mitapivat or a pharmaceutically acceptable salt thereof is formulated for administration at a dose equivalent to about 140 mg of mitapivat thereof once per day. In another aspect, mitapivat or a pharmaceutically acceptable salt thereof is formulated for administration at a dose equivalent to about 150 mg of mitapivat thereof once per day. In another aspect, mitapivat or a pharmaceutically acceptable salt thereof is formulated for administration at a dose equivalent to about 160 mg to about 200 mg of mitapivat thereof once per day. In another aspect, mitapivat or a pharmaceutically acceptable salt thereof is formulated for administration at a dose equivalent to about 200 mg to about 360 mg of mitapivat thereof once per day. In one aspect, mitapivat or a pharmaceutically acceptable salt thereof is formulated for administration at a dose equivalent to about 5 mg of mitapivat once every other day. In one aspect, mitapivat or a pharmaceutically acceptable salt thereof is formulated for administration at a dose equivalent to about 20 mg of mitapivat once every other day. In one aspect, mitapivat or a pharmaceutically acceptable salt thereof is formulated for administration at a dose equivalent to about 50 mg of mitapivat once every other day. In one aspect, mitapivat or a pharmaceutically acceptable salt thereof is formulated for administration at a dose equivalent to about 100 mg of mitapivat once every other day. In certain embodiment, the pharmaceutically acceptable salt of mitapivat is mitapivat sulfate.

In certain embodiments, for any of the methods presented herein, further comprising reducing the dose of mitapivat or a pharmaceutically acceptable salt thereof by about 70% to about 80%. In certain embodiments, for any of the methods presented herein, further comprising reducing the dose of mitapivat or a pharmaceutically acceptable salt thereof by about 60% to about 70%. In certain embodiments, for any of the methods presented herein, further comprising reducing the dose of mitapivat or a pharmaceutically acceptable salt thereof by about 50% to about 60%. In certain embodiments, for any of the methods presented herein, further comprising reducing the dose of mitapivat or a pharmaceutically acceptable salt thereof by about 40% to about 50%. In certain embodiments, for any of the methods presented herein, further comprising reducing the dose of mitapivat or a pharmaceutically acceptable salt thereof by about 30% to about 40%. In certain embodiments, for any of the methods presented herein, further comprising reducing the dose of mitapivat or a pharmaceutically acceptable salt thereof by about 20% to about 30%. In certain embodiments, for any of the methods presented herein, further comprising reducing the dose of mitapivat or a pharmaceutically acceptable salt thereof by about 10% to about 20%. In certain embodiments, for any of the methods presented herein, further comprising reducing the dose of mitapivat or a pharmaceutically acceptable salt thereof by about 50%. In certain embodiments, for any of the methods presented herein, further comprising reducing the dose of mitapivat or a pharmaceutically acceptable salt thereof from the dose equivalent to about 400 mg of mitapivat to the dose equivalent to about 200 mg. In certain embodiments, for any of the methods presented herein, further comprising reducing the dose of mitapivat or a pharmaceutically acceptable salt thereof from the dose equivalent to about 300 mg of mitapivat to the dose equivalent to about 150 mg. In certain embodiments, for any of the methods presented herein, further comprising reducing the dose of mitapivat or a pharmaceutically acceptable salt thereof from the dose equivalent to about 200 mg of mitapivat to the dose equivalent to about 100 mg. In certain embodiments, for any of the methods presented herein, further comprising reducing the dose of mitapivat or a pharmaceutically acceptable salt thereof from the dose equivalent to about 100 mg of mitapivat to the dose equivalent to about 50 mg. In certain embodiments, for any of the methods presented herein, further comprising reducing the dose of mitapivat or a pharmaceutically acceptable salt thereof from the dose equivalent to about 50 mg of mitapivat to the dose equivalent to about 25 mg. In certain embodiments, for any of the methods presented herein, further comprising reducing the dose of mitapivat or a pharmaceutically acceptable salt thereof from the dose equivalent to about 20 mg of mitapivat to the dose equivalent to about 10 mg. In certain embodiments, for any of the methods presented herein, further comprising reducing the dose of mitapivat or a pharmaceutically acceptable salt thereof from the dose equivalent to about 10 mg of mitapivat to the dose equivalent to about 5 mg. In certain embodiments, for any of the methods presented herein, further comprising reducing the dose of mitapivat or a pharmaceutically acceptable salt thereof from the dose equivalent to about 5 mg of mitapivat to the dose equivalent to about 2.5 mg.

In certain embodiments, for any of the methods presented herein, further comprising reducing the dose frequency of mitapivat or a pharmaceutically acceptable salt thereof by about 70% to about 80%. In certain embodiments, for any of the methods presented herein, further comprising reducing the dose frequency of mitapivat or a pharmaceutically acceptable salt thereof by about 60% to about 70%. In certain embodiments, for any of the methods presented herein, further comprising reducing the dose frequency of mitapivat or a pharmaceutically acceptable salt thereof by about 50% to about 60%. In certain embodiments, for any of the methods presented herein, further comprising reducing the dose frequency of mitapivat or a pharmaceutically acceptable salt thereof by about 40% to about 50%. In certain embodiments, for any of the methods presented herein, further comprising reducing the dose frequency of mitapivat or a pharmaceutically acceptable salt thereof by about 30% to about 40%. In certain embodiments, for any of the methods presented herein, further comprising reducing the dose frequency of mitapivat or a pharmaceutically acceptable salt thereof by about 20% to about 30%. In certain embodiments, for any of the methods presented herein, further comprising reducing the dose frequency of mitapivat or a pharmaceutically acceptable salt thereof by about 10% to about 20%. In certain embodiments, for any of the methods presented herein, further comprising reducing the dose frequency of mitapivat or a pharmaceutically acceptable salt thereof by about 50%. In certain embodiments, for any of the methods presented herein, further comprising reducing the dose frequency of mitapivat or a pharmaceutically acceptable salt thereof from twice daily to once daily. In certain embodiments, for any of the methods presented herein, further comprising reducing the dose frequency of mitapivat or a pharmaceutically acceptable salt thereof from once daily to once every other day.

In certain embodiments, for any of the methods presented herein, further comprising reducing the dose of mitapivat or a pharmaceutically acceptable salt thereof from the dose equivalent to about 400 mg of mitapivat twice daily to the dose equivalent to about 200 mg twice daily. In certain embodiments, for any of the methods presented herein, further comprising reducing the dose of mitapivat or a pharmaceutically acceptable salt thereof from the dose equivalent to about 300 mg of mitapivat twice daily to the dose equivalent to about 150 mg twice daily. In certain embodiments, for any of the methods presented herein, further comprising reducing the dose of mitapivat or a pharmaceutically acceptable salt thereof from the dose equivalent to about 200 mg of mitapivat twice daily to the dose equivalent to about 100 mg twice daily. In certain embodiments, for any of the methods presented herein, further comprising reducing the dose of mitapivat or a pharmaceutically acceptable salt thereof from the dose equivalent to about 100 mg of mitapivat twice daily to the dose equivalent to about 50 mg twice daily. In certain embodiments, for any of the methods presented herein, further comprising reducing the dose of mitapivat or a pharmaceutically acceptable salt thereof from the dose equivalent to about 50 mg of mitapivat twice daily to the dose equivalent to about 25 mg twice daily. In certain embodiments, for any of the methods presented herein, further comprising reducing the dose of mitapivat or a pharmaceutically acceptable salt thereof from the dose equivalent to about 20 mg of mitapivat twice daily to the dose equivalent to about 10 mg twice daily. In certain embodiments, for any of the methods presented herein, further comprising reducing the dose of mitapivat or a pharmaceutically acceptable salt thereof from the dose equivalent to about 10 mg of mitapivat twice daily to the dose equivalent to about 5 mg twice daily. In certain embodiments, for any of the methods presented herein, further comprising reducing the dose of mitapivat or a pharmaceutically acceptable salt thereof from the dose equivalent to about 5 mg twice daily of mitapivat to the dose equivalent to about 2.5 mg twice daily.

In certain embodiments, for any of the methods presented herein, further comprising reducing the dose of mitapivat or a pharmaceutically acceptable salt thereof from the dose equivalent to about 400 mg of mitapivat once daily to the dose equivalent to about 200 mg once daily. In certain embodiments, for any of the methods presented herein, further comprising reducing the dose of mitapivat or a pharmaceutically acceptable salt thereof from the dose equivalent to about 300 mg of mitapivat once daily to the dose equivalent to about 150 mg once daily. In certain embodiments, for any of the methods presented herein, further comprising reducing the dose of mitapivat or a pharmaceutically acceptable salt thereof from the dose equivalent to about 200 mg of mitapivat once daily to the dose equivalent to about 100 mg once daily. In certain embodiments, for any of the methods presented herein, further comprising reducing the dose of mitapivat or a pharmaceutically acceptable salt thereof from the dose equivalent to about 100 mg of mitapivat once daily to the dose equivalent to about 50 mg once daily. In certain embodiments, for any of the methods presented herein, further comprising reducing the dose of mitapivat or a pharmaceutically acceptable salt thereof from the dose equivalent to about 50 mg of mitapivat once daily to the dose equivalent to about 25 mg once daily. In certain embodiments, for any of the methods presented herein, further comprising reducing the dose of mitapivat or a pharmaceutically acceptable salt thereof from the dose equivalent to about 20 mg of mitapivat once daily to the dose equivalent to about 10 mg once daily. In certain embodiments, for any of the methods presented herein, further comprising reducing the dose of mitapivat or a pharmaceutically acceptable salt thereof from the dose equivalent to about 10 mg of mitapivat once daily to the dose equivalent to about 5 mg once daily. In certain embodiments, for any of the methods presented herein, further comprising reducing the dose of mitapivat or a pharmaceutically acceptable salt thereof from the dose equivalent to about 5 mg once daily of mitapivat to the dose equivalent to about 2.5 mg once daily.

In certain embodiments, for any of the methods presented herein, further comprising reducing the dose of mitapivat or a pharmaceutically acceptable salt thereof from the dose equivalent to about 400 mg of mitapivat twice daily to the dose equivalent to about 200 mg once daily. In certain embodiments, for any of the methods presented herein, further comprising reducing the dose of mitapivat or a pharmaceutically acceptable salt thereof from the dose equivalent to about 300 mg of mitapivat twice daily to the dose equivalent to about 150 mg once daily. In certain embodiments, for any of the methods presented herein, further comprising reducing the dose of mitapivat or a pharmaceutically acceptable salt thereof from the dose equivalent to about 200 mg of mitapivat twice daily to the dose equivalent to about 100 mg once daily. In certain embodiments, for any of the methods presented herein, further comprising reducing the dose of mitapivat or a pharmaceutically acceptable salt thereof from the dose equivalent to about 100 mg of mitapivat twice daily to the dose equivalent to about 50 mg once daily. In certain embodiments, for any of the methods presented herein, further comprising reducing the dose of mitapivat or a pharmaceutically acceptable salt thereof from the dose equivalent to about 50 mg of mitapivat twice daily to the dose equivalent to about 25 mg once daily. In certain embodiments, for any of the methods presented herein, further comprising reducing the dose of mitapivat or a pharmaceutically acceptable salt thereof from the dose equivalent to about 20 mg of mitapivat twice daily to the dose equivalent to about 10 mg once daily. In certain embodiments, for any of the methods presented herein, further comprising reducing the dose of mitapivat or a pharmaceutically acceptable salt thereof from the dose equivalent to about 10 mg of mitapivat twice daily to the dose equivalent to about 5 mg once daily. In certain embodiments, for any of the methods presented herein, further comprising reducing the dose of mitapivat or a pharmaceutically acceptable salt thereof from the dose equivalent to about 5 mg twice daily of mitapivat to the dose equivalent to about 2.5 mg once daily.

In some embodiments, mitapivat or a pharmaceutically acceptable salt thereof (e.g., mitapivat sulfate) is present in the tablet composition in an amount equivalent to about 1 to about 200 mg of mitapivat. In some embodiments, mitapivat or a pharmaceutically acceptable salt thereof (e.g., mitapivat sulfate) is present in the tablet composition in an amount equivalent to about 1 to about 150 mg of mitapivat. In some embodiments, mitapivat or a pharmaceutically acceptable salt thereof (e.g., mitapivat sulfate) is present in the tablet composition in an amount equivalent to about 1 to about 100 mg of mitapivat. In some embodiments, mitapivat or a pharmaceutically acceptable salt thereof (e.g., mitapivat sulfate) is present in the tablet composition in an amount equivalent to about 5 mg of mitapivat. In some embodiments, mitapivat or a pharmaceutically acceptable salt thereof (e.g., mitapivat sulfate) is present in the tablet composition in an amount equivalent to about 20 mg of mitapivat. In some embodiments, mitapivat or a pharmaceutically acceptable salt thereof (e.g., mitapivat sulfate) is present in the tablet composition in an amount equivalent to about 50 mg of mitapivat. In some embodiments, mitapivat or a pharmaceutically acceptable salt thereof (e.g., mitapivat sulfate) is present in the tablet composition in an amount equivalent to about 75 mg of mitapivat. In some embodiments, mitapivat or a pharmaceutically acceptable salt thereof (e.g., mitapivat sulfate) is present in a tablet composition in an amount equivalent to about 100 mg of mitapivat. In certain embodiment, the pharmaceutically acceptable salt of mitapivat is mitapivat sulfate.

As used herein, the dose amount of mitapivat or a pharmaceutically acceptable salt thereof (e.g., mitapivat sulfate) is based on the equivalence to the free-base form of mitapivat. For example, "mitapivat or pharmaceutically acceptable salt thereof present in the composition in an amount equivalent to about 2.0 mg of mitapivat" means about 2.0 mg of free-base mitapivat or about 2.33 mg of mitapivat sulfate having the structural formula as depicted in the background of the present disclosure.

Methods of Treatment (Mitapivat Monotherapy and Concomitant Medications)

In one aspect, the present disclosure provides methods of treating a disease, disorder or condition with mitapivat or a pharmaceutically acceptable salt thereof and a CYP3A4/5 inducer or a CYP3A4/5 inhibitor or a p-gp inhibitor; use of mitapivat and a CYP3A4/5 inducer or a CYP3A4/5 inhibitor or a p-gp inhibitor for the manufacture of a medicament for treating a disease, disorder or condition; and mitapivat or a pharmaceutically acceptable salt thereof and a CYP3A4/5 inducer or a CYP3A4/5 inhibitor or a p-gp inhibitor for use in treating a disease, disorder or condition. The disease, disorder or condition treated is pyruvate kinase deficiency (PKD), sickle cell disease, or thalassemia as further discussed in the following embodiments, and any one disease, disorder or condition described in the section "Diseases, Disorders and Conditions" provided in the present disclosure.

In one embodiment, the present disclosure relates to a method of treating pyruvate kinase deficiency (PKD) in a subject, comprising administering to the subject an effective amount of mitapivat or a pharmaceutically acceptable salt thereof and an effective amount of an inducer of cytochrome P450 3A4 (CYP3A4) or 3A5 (CYP3A5).

In another embodiment, the present disclosure relates to a method of treating sickle cell disease in a subject, comprising administering to the subject an effective amount of mitapivat or a pharmaceutically acceptable salt thereof and an effective amount of an inducer of cytochrome P450 3A4 (CYP3A4) or 3A5 (CYP3A5).

In yet another embodiment, the present disclosure relates to a method of treating thalassemia in a subject, comprising administering to the subject an effective amount of mitapivat or a pharmaceutically acceptable salt thereof and an effective amount of an inducer of cytochrome P450 3A4 (CYP3A4) or 3A5 (CYP3A5). In certain embodiments, the thalassemia is alpha thalassemia. In certain embodiments, the thalassemia is beta thalassemia.

In one embodiment, the method of any one of the preceding embodiments further comprises:
(a) monitoring the subject for an effect of a drug-drug interaction between mitapivat or a pharmaceutically acceptable salt thereof and the CYP3A4/5 inducer; and
(b) in the event that an effect of the drug-drug interaction is present, adjusting the effective amount of mitapivat or a pharmaceutically acceptable salt thereof and/or the effective amount of the CYP3A4/5 inducer being administered to the subject to reduce the effect.

In some embodiments, the adjustment is to reduce the dose of mitapivat or a pharmaceutically acceptable salt thereof. In some embodiments, the adjustment is to reduce the dose frequency of mitapivat or a pharmaceutically acceptable salt thereof. In some embodiments, the adjustment is to reduce the dose and dose frequency of mitapivat or a pharmaceutically acceptable salt thereof. Details of the dose and/or dose frequency adjustment are shown in the dose and dose regime section.

In one embodiment, the method of the preceding embodiment further comprises:
(c) repeating (a) and (b) until there are no further detectable symptoms of the drug-drug interaction.

Steps (a) and (b) can be repeated as many times as necessary until there are no further detectable symptoms of the drug-drug interaction. In one embodiment, step (a) comprises measuring and analyzing the pharmacokinetic (PK) such as AUC (i.e., area under the plasma concentration-time curve, such as $AUC_{0-24}$, $AUC_{0-t}$, $AUC_{0-inf}$, $AUC_{\%estrap}$) and $C_{max}$ values (i.e., the maximum (or peak) serum concentration that a drug achieves in a specified compartment or test area of the body after the drug has been administrated and before the administration of a second dose). In one embodiment, step (a) comprises measuring and analyzing other PK parameters such as but not limited to $C_L/F$ (i.e., apparent total body clearance of the drug from plasma), $V_z/F$ (i.e., apparent volume of distribution during terminal phase after non-intravenous administration), $t_{1/2}$ (elimination half-life), $t_{last}$, $t_{max}$ (time to reach maximum (peak) plasma concentration following drug administration), etc.

A "drug-drug interaction" as used herein refers to a change in concentration in a patient of a first drug (e.g., mitapivat) and consequential change in the effect of the first drug on the subject/patient resulting from administration of a second drug (e.g., a CYP3A4/5 inducer, a CYP3A4/5 inhibitor). The change in concentration and consequential change in effect of the first drug resulting from the second drug typically occurs because of a change in activity or expression level of a detoxification enzyme that acts to clear the first drug from the patient (such as CYP3A4/5), wherein the change in activity or expression level of the detoxification enzyme is caused by the second drug. An increase in activity or expression level of the detoxification enzyme will tend to decrease the concentration of the first drug in the patient and its consequential effect on the patient, whereas a decrease in activity or expression level of the detoxification enzyme will tend to increase the concentration of the first drug in the patient and its consequential effect on the patient.

An "effect of a drug-drug interaction" as used herein refers to a detectable and measurable effect, such as a detectable symptom, on the subject/patient caused by the drug-drug interaction. Where the concentration of the first drug is increased, such as when mitapivat is co-administered with a CYP3A4/5 inhibitor, the "effect" typically refers to undesired phenomena such as an overdose of the first drug, liver failure, kidney failure, and the prevalence of side effects and adverse reactions. Where the concentration of the first drug is decreased, such as when mitapivat is co-administered with a CYP3A4/5 inducer, the "effect" typically refers to a decrease in the therapeutic efficacy of the first drug (e.g., mitapivat). Exemplary effects of a drug-drug interaction as used herein further include headache, insomnia, nausea, viral upper respiratory tract infection, arthralgia, diarrhoea, fatigue, hot flush, influenza, vomiting, cough, dizziness, oropharyngeal pain, pyrexia, back pain, dysmenorrhoea, and gastroenteritis, and dyspepsia, hypertriglyceridemia, hemolytic anemia, hemolysis, dizziness, etc.

In one embodiment, the present disclosure relates to a method of treating pyruvate kinase deficiency (PKD) in a subject, comprising administering to the subject an effective amount of mitapivat or a pharmaceutically acceptable salt thereof and an effective amount of an inhibitor of cytochrome P450 3A4 (CYP3A4) or 3A5 (CYP3A5).

In another embodiment, the present disclosure relates to a method of treating sickle cell disease in a subject, comprising administering to the subject an effective amount of mitapivat or a pharmaceutically acceptable salt thereof and an effective amount of an inhibitor of cytochrome P450 3A4 (CYP3A4) or 3A5 (CYP3A5).

In yet another embodiment, the present disclosure relates to a method of treating thalassemia in a subject, comprising administering to the subject an effective amount of mitapivat or a pharmaceutically acceptable salt thereof and an effective amount of an inhibitor of cytochrome P450 3A4 (CYP3A4) or 3A5 (CYP3A5) or a p-gp inhibitor. In certain embodiments, the thalassemia is alpha thalassemia. In certain embodiments, the thalassemia is beta thalassemia.

In one embodiment, the method of any one of the suitable preceding embodiments further comprises:
(a) monitoring the subject for a symptom of a drug-drug interaction between mitapivat or a pharmaceutically acceptable salt thereof and the CYP3A4/5 inhibitor; and
(b) in the event that a symptom of the drug-drug interaction is present, adjusting the effective amount of mitapivat or a pharmaceutically acceptable salt thereof and/or the effective amount of the CYP3A4/5 inhibitor being administered to the subject to reduce the effect.

In some embodiments, the adjustment is to reduce the dose of mitapivat or a pharmaceutically acceptable salt thereof. In some embodiments, the adjustment is to reduce the dose frequency of mitapivat or a pharmaceutically acceptable salt thereof. In some embodiments, the adjustment is to reduce the dose and dose frequency of mitapivat or a pharmaceutically acceptable salt thereof. Details of the dose and/or dose frequency adjustment are shown in the dose and dose regime section.

In one embodiment, the method of the preceding embodiment further comprises:
(c) repeating (a) and (b) until there are no further detectable symptoms of the drug-drug interaction.

Likewise, steps (a) and (b) can be repeated as many times as necessary until here are no further detectable symptoms of the drug-drug interaction. Ways of monitoring the subject for a symptom of a drug-drug interaction between mitapivat or a pharmaceutically acceptable salt thereof and the CYP3A4/5 inhibitor as recited in step (a) are as described above.

In one embodiment, the method of any one of the preceding embodiments comprises administering to the subject the effective amount of mitapivat or a pharmaceutically acceptable salt thereof and the effective amount of the CYP3A4/5 inducer (or inhibitor) sequentially.

In one embodiment, the method of any one of the preceding embodiments comprises administering to the subject the effective amount of mitapivat or a pharmaceutically acceptable salt thereof and the effective amount of the CYP3A4/5 inducer (or inhibitor) concurrently.

In one embodiment, the method of any one of the preceding embodiments comprises administering to the subject the effective amount of mitapivat or a pharmaceutically acceptable salt thereof and the effective amount of the CYP3A4/5 inducer (or inhibitor) sequentially and concurrently. As used herein, "co-administered" or "in combination with" encompasses administration of mitapivat or a pharmaceutically acceptable salt thereof and the CYP3A4/5 inducer (or inhibitor) sequentially and concurrently, or at different intervals. In another embodiments, for the method of any one of the embodiments, the CYP3A4/5 inducer is a mild CYP3A4/5 inducer. In another embodiments, for the method of any one of the embodiments, the CYP3A4/5 inhibitor is a mild CYP3A4/5 inhibitor. In another embodiments, for the methods of any one of the embodiments, the CYP3A4/5 inhibitor is a moderate CYP3A4/5 inhibitor.

In another aspect, the present disclosure provides methods of treating a disease, disorder or a condition with mitapivat in the absence of a CYP3A4/5 inducer or a CYP3A4/5 inhibitor or a p-gp inhibitor; use of mitapivat in the absence of a CYP3A4/5 inducer or a CYP3A4/5 inhibitor or a p-gp inhibitor for the manufacture of a medicament for treating disease, disorder or a condition; and mitapivat in the absence of a CYP3A4/5 inducer or a CYP3A4/5 inhibitor or a p-gp inhibitor for use in treating a disease, disorder or a condition.

As used herein, "in the absence of" when referring to a secondary drug co-administered with mitapivat (e.g., a CYP3A4/5 inducer or a CYP3A4/5 inhibitor or a p-gp inhibitor), refers to levels of the secondary drug in the subject/patient that are sufficiently low that such that any change in the levels of the detoxification enzymes for mitapivat and the secondary drug results in no detectable symptoms of a drug-drug interaction between mitapivat and the secondary drug.

In one embodiment, the present disclosure relates to a method of treating pyruvate kinase deficiency (PKD) in a subject, comprising administering to the subject an effective amount of mitapivat or a pharmaceutically acceptable salt thereof in the absence of an inducer of cytochrome P450 3A4 (CYP3A4) or 3A5 (CYP3A5).

In another embodiment, the present disclosure relates to a method of treating sickle cell disease in a subject, comprising administering to the subject an effective amount of mitapivat or a pharmaceutically acceptable salt thereof in the absence of an inducer of cytochrome P450 3A4 (CYP3A4) or 3A5 (CYP3A5).

In yet another embodiment, the present disclosure relates to a method of treating thalassemia in a subject, comprising administering to the subject an effective amount of mitapivat or a pharmaceutically acceptable salt thereof in the absence of an inducer of cytochrome P450 3A4 (CYP3A4) or 3A5 (CYP3A5). In some embodiments, the thalassemia is alpha thalassemia. In some embodiments, the thalassemia is beta thalassemia.

In one embodiment, in accordance with the method of any one of the suitable preceding embodiments, administration of a CYP3A4/5 inducer, if any, is terminated at a sufficient time interval prior to the administration of the effective amount of mitapivat or a pharmaceutically acceptable salt thereof such that there is no detectable symptom of a drug-drug interaction between mitapivat or a pharmaceutically acceptable salt thereof and the CYP3A4/5 inducer. In certain embodiments, the CYP3A4/5 inducer is a strong CYP3A4/5 inducer. In certain embodiments, the CYP3A4/5 inducer is a moderate CYP3A4/5 inducer. In some embodiments, the CYP3A4/5 inducer is terminated at least 30 days prior to the administration of the effective amount of mitapivat or a pharmaceutically acceptable salt thereof. In some embodiments, the CYP3A4/5 inducer is terminated at least 28 days prior to the administration of the effective amount of mitapivat or a pharmaceutically acceptable salt thereof. In some embodiments, the CYP3A4/5 inducer is terminated at least 25 days prior to the administration of the effective amount of mitapivat or a pharmaceutically acceptable salt thereof. In some embodiments, the CYP3A4/5 inducer is terminated at least 21 days prior to the administration of the effective amount of mitapivat or a pharmaceutically acceptable salt thereof. In some embodiments, the CYP3A4/5 inducer is terminated at least 15 days prior to the administration of the effective amount of mitapivat or a pharmaceutically acceptable salt thereof. In some embodiments, the CYP3A4/5 inducer is terminated at least 14 days prior to the administration of the effective amount of mitapivat or a pharmaceutically acceptable salt thereof. In some embodiments, the CYP3A4/5 inducer is terminated at least 10 days prior to the administration of the effective amount of mitapivat or a pharmaceutically acceptable salt thereof. In some embodiments, the CYP3A4/5 inducer is terminated at least 7 days prior to the administration of the effective amount of mitapivat or a pharmaceutically acceptable salt thereof. In some embodiments, the CYP3A4/5 inducer is terminated at least 5 days prior to the administration of the effective amount of mitapivat or a pharmaceutically acceptable salt thereof.

In one embodiment, the present disclosure relates to a method of treating pyruvate kinase deficiency (PKD) in a subject, comprising administering to the subject an effective amount of mitapivat or a pharmaceutically acceptable salt thereof in the absence of an inhibitor of cytochrome P450 3A4 (CYP3A4) or 3A5 (CYP3A5).

In another embodiment, the present disclosure relates to a method of treating sickle cell disease in a subject, comprising administering to the subject an effective amount of mitapivat or a pharmaceutically acceptable salt thereof in the absence of an inhibitor of cytochrome P450 3A4 (CYP3A4) or 3A5 (CYP3A5).

In yet another embodiment, the present disclosure relates to a method of treating thalassemia in a subject, comprising administering to the subject an effective amount of mitapivat or a pharmaceutically acceptable salt thereof in the absence of an inhibitor of cytochrome P450 3A4 (CYP3A4) or 3A5 (CYP3A5). In certain embodiment, the thalassemia is alpha-thalassemia. In certain embodiment, the thalassemia is beta-thalassemia.

In one embodiment, in accordance with the method of any one of the suitable preceding embodiments, administration of a CYP3A4/5 inhibitor, if any, is terminated at a sufficient time interval prior to the administration of the effective amount of mitapivat or a pharmaceutically acceptable salt thereof such that there is no detectable symptom of a drug-drug interaction between mitapivat or a pharmaceutically acceptable salt thereof and the CYP3A4/5 inhibitor. In certain embodiments, the CYP3A4/5 inhibitor is a strong CYP3A4/5 inhibitor. In certain embodiments, the CYP3A4/5 inhibitor is a moderate CYP3A4/5 inhibitor. In some embodiments, the CYP3A4/5 inhibitor is terminated at least 21 days prior to the administration of the effective amount of mitapivat or a pharmaceutically acceptable salt thereof. In some embodiments, the CYP3A4/5 inhibitor is terminated at least 15 days prior to the administration of the effective amount of mitapivat or a pharmaceutically acceptable salt thereof. In some embodiments, the CYP3A4/5 inhibitor is terminated at least 14 days prior to the administration of the effective amount of mitapivat or a pharmaceutically acceptable salt thereof. In some embodiments, the CYP3A4/5 inhibitor is terminated at least 10 days prior to the administration of the effective amount of mitapivat or a pharmaceutically acceptable salt thereof. In some embodiments, the CYP3A4/5 inhibitor is terminated at least 7 days prior to the administration of the effective amount of mitapivat or a pharmaceutically acceptable salt thereof. In some embodiments, the CYP3A4/5 inhibitor is terminated at least 5 days prior to the administration of the effective amount of mitapivat or a pharmaceutically acceptable salt thereof. In some embodiments, the CYP3A4/5 inhibitor is terminated at least 3 days prior to the administration of the effective amount of mitapivat or a pharmaceutically acceptable salt thereof. In some embodiments, the CYP3A4/5 inhibitor is terminated at least 2 days prior to the administration of the effective amount of mitapivat or a pharmaceutically acceptable salt thereof. In some embodiments, the CYP3A4/5 inhibitor is terminated at least 1 day prior to the administration of the effective amount of mitapivat or a pharmaceutically acceptable salt thereof.

In one embodiment, the present disclosure relates to a method of treating pyruvate kinase deficiency (PKD) in a subject, comprising administering to the subject an effective amount of mitapivat or a pharmaceutically acceptable salt thereof in the absence of a p-gp inhibitor.

In another embodiment, the present disclosure relates to a method of treating sickle cell disease in a subject, comprising administering to the subject an effective amount of mitapivat or a pharmaceutically acceptable salt thereof in the absence of a p-gp inhibitor.

In yet another embodiment, the present disclosure relates to a method of treating thalassemia in a subject, comprising administering to the subject an effective amount of mitapivat or a pharmaceutically acceptable salt thereof in the absence of a p-gp inhibitor. In certain embodiment, the thalassemia is alpha-thalassemia. In certain embodiment, the thalassemia is beta-thalassemia.

In one embodiment, in accordance with the method of any one of the suitable preceding embodiments, administration of a p-gp inhibitor, if any, is terminated at a sufficient time interval prior to the administration of the effective amount of mitapivat or a pharmaceutically acceptable salt thereof such that there is no detectable symptom of a drug-drug interaction between mitapivat or a pharmaceutically acceptable salt thereof and the p-gp inhibitor. In certain embodiments, the p-gp inhibitor is a strong p-gp inhibitor (e.g. amiodarone, azithromycin, captopril, carvedilol, clarithromycin, conivaptan, cyclosporine, diltiazem, dronedarone, erythromycin, felodipine, itraconazole, ketoconazole, lopinavir, ritonavir, quercetin, quinidine, ranolazine ticagrelor, and erapamil). In some embodiments, the p-gp inhibitor inhibitor is terminated at least 21 days prior to the administration of the effective amount of mitapivat or a pharmaceutically acceptable salt thereof. In some embodiments, the p-gp inhibitor is terminated at least 15 days prior to the administration of the effective amount of mitapivat or a pharmaceutically acceptable salt thereof. In some embodiments, the p-gp inhibitor is terminated at least 14 days prior to the administration of the effective amount of mitapivat or a pharmaceutically acceptable salt thereof. In some embodiments, the p-gp inhibitor is terminated at least 10 days prior to the administration of the effective amount of mitapivat or a pharmaceutically acceptable salt thereof. In some embodiments, the p-gp inhibitor is terminated at least 7 days prior to the administration of the effective amount of mitapivat or a pharmaceutically acceptable salt thereof. In some embodiments, the p-gp inhibitor is terminated at least 5 days prior to the administration of the effective amount of mitapivat or a pharmaceutically acceptable salt thereof. In some embodiments, the p-gp inhibitor is terminated at least 3 days prior to the administration of the effective amount of mitapivat or a pharmaceutically acceptable salt thereof. In some embodiments, the p-gp inhibitor is terminated at least 2 days prior to the administration of the effective amount of mitapivat or a pharmaceutically acceptable salt thereof. In some embodiments, the p-gp inhibitor is terminated at least 1 day prior to the administration of the effective amount of mitapivat or a pharmaceutically acceptable salt thereof.

In one embodiment, the method of any one of the preceding embodiments comprises administering to the subject about 1 mg to about 2500 mg, or about 5 mg to 2500 mg, or about 30 mg to 2500 mg, or about 5 mg to about 700 mg, or about 15 mg to about 700 mg, about 5 mg to about 360 mg, about 5 mg to about 300 mg, about 50 mg to about 300 mg, about 120 mg to about 360 mg, about 120 mg to about 300 mg, about 5 mg to about 120 mg, about 5 mg, about 20 mg, about 50 mg, about 100 mg, about 120 mg , about 200 mg, about 300 mg, or about 360 mg of mitapivat or a pharmaceutically acceptable salt thereof.

In one embodiment, the method of any one of the preceding embodiments comprises administering to the subject about 1 mg to about 2500 mg of mitapivat or a pharmaceutically acceptable salt thereof.

In one embodiment, the method of any one of the preceding embodiments comprises administering to the subject about 5 mg to 2500 mg of mitapivat or a pharmaceutically acceptable salt thereof.

In one embodiment, the method of any one of the preceding embodiments comprises administering to the subject about 5 mg to about 360 mg of mitapivat or a pharmaceutically acceptable salt thereof.

In one embodiment, the method of any one of the preceding embodiments comprises administering to the subject about 5 mg to about 300 mg of mitapivat or a pharmaceutically acceptable salt thereof.

In one embodiment, the method of any one of the preceding embodiments comprises administering to the subject about 50 mg to about 300 mg of mitapivat or a pharmaceutically acceptable salt thereof.

In one embodiment, the method of any one of the preceding embodiments comprises administering to the subject about 5 mg of mitapivat or a pharmaceutically acceptable salt thereof.

In one embodiment, the method of any one of the preceding embodiments comprises administering to the subject about 20 mg of mitapivat or a pharmaceutically acceptable salt thereof.

In one embodiment, the method of any one of the preceding embodiments comprises administering to the subject about 50 mg of mitapivat or a pharmaceutically acceptable salt thereof.

In one embodiment, the method of any one of the preceding embodiments comprises administering to the subject about 100 mg of mitapivat or a pharmaceutically acceptable salt thereof.

In one embodiment, the method of any one of the preceding embodiments comprises administering to the subject the effective amount of mitapivat or a pharmaceutically acceptable salt thereof once daily.

In one embodiment, the method of any one of the preceding embodiments comprises administering to the subject the effective amount of mitapivat or a pharmaceutically acceptable salt thereof twice daily.

In one embodiment, the method of any one of the preceding embodiments comprises administering to the subject a sulfate salt of mitapivat, such as a sulfate salt of mitapivat having the structural formula depicted in the background of the present disclosure.

In one embodiment, in the method of any one of the suitable preceding embodiments, the CYP3A4/5 inducer is a strong inducer of CYP3A4/5.

In one embodiment, in the method of any one of the suitable preceding embodiments, the CYP3A4/5 inducer is a moderate inducer of CYP3A4/5.

In one embodiment, in the method of any one of the suitable preceding embodiments, the CYP3A4/5 inducer is a mild inducer of CYP3A4/5.

In one embodiment, in the method of any one of the suitable preceding embodiments, the inducer of CYP3A4/5 is a strong CYP3A4/5 inducer selected from a group consisting of apalutamide, enzalutamide, mitotane, phenytoin, efavirenz, nevirapine, carbamazepine, glucocorticoids, modafinil, oxcarbazepine, phenobarbital, henytoin, pioglitazone, rifabutin, rifampin, St. John's Wort, and troglitazone.

In one embodiment, in the method of any one of the suitable preceding embodiments, the inducer of CYP3A4/5 is a moderate CYP3A4/5 inducer selected from a group consisting of bosentan, etravirine, phenobarbital, and primidone.

In one embodiment, in the method of any one of the suitable preceding embodiments, the inducer of CYP3A4/5 is a mild CYP3A4/5 inducer selected from a group consisting of armodafinil, modafinil, and rufinamide.

In one embodiment, in the method of any one of the suitable preceding embodiments, the CYP3A4/5 inducer is selected from the group consisting of aminoglutethimide, bexarotene, bosentan, carbamazepine, dexamethasone, efavirenz, fosphenytoin, griseofulvin, modafinil, nafcillin, nevirapine, oxcarbazepine, phenobarbital, phenytoin, primidone, rifabutin, rifampin, rifapentine, St. John's Wort, avasimibe, dabrafenib, mifepristone, etravirine, armodafninil, glycerol phenylbutyrate, asunaprevir, rifunamide, oritavancin, clobazam, felbamate, eslicarbazepine acetate, and genistein.

In one embodiment, in the method of any one of the suitable preceding embodiments, the CYP3A4/5 inducer is rifampin. In one aspect, rifampin is administered to the subject in the form of a capsule composition. In one aspect, about 0.1-1000 mg of rifampin is administered to the subject. In one aspect, about 100-1000 mg of rifampin is administered to the subject.

In one embodiment, the method of any one of the suitable preceding embodiments comprises administering about 600 mg of rifampin to the subject. In one aspect, the method of any one of the suitable preceding embodiments comprises administering about 600 mg of rifampin to the subject once daily.

In one embodiment, in the method of any one of the suitable preceding embodiments, the inhibitor of CYP3A4/5 is a strong inhibitor of CYP3A4/5.

In one embodiment, in the method of any one of the suitable preceding embodiments, the inhibitor of CYP3A4/5 is a moderate inhibitor of CYP3A4/5.

In one embodiment, in the method of any one of the suitable preceding embodiments, the inhibitor of CYP3A4/5 is a mild inhibitor of CYP3A4/5.

In one embodiment, in the method of any one of the suitable preceding embodiments, the inhibitor of CYP3A4/5 is selected from the group consisting of toamiodarone, amprenavir, aprepitant, atazanavir, chloramphenicol, clarithromycin, conivaptan, cyclosporine, darunavir, dasatinib, delavirdine, diltiazem, erythromycin, fluconazole, fluoxetine, fluvoxamine, fosamprenavir, imatinib, indinavir, isoniazid, itraconazole, ketoconazole, lapatinib, miconazole, nefazodone, nelfinavir, posaconazole, ritonavir, quinupristin, saquinavir, tamoxifen, telithromycin, troleandomycin, verapamil, voriconazole, grapefruit, Seville oranges, limes, pomelos, fruit juices, and vegetables from mustard green family.

In one embodiment, in the method of any one of the suitable preceding embodiments, the inhibitor of CYP3A4/5 is a strong CYP3A4/5 inhibitor selected from a group consisting of boceprevir, cobicistat, danoprevir, elvitegravir, ritonavir, grapefruit juice, indinavir, itraconazole, ketoconazole, lopinavir, paritaprevir, ombitasvir, dasabuvir, posaconazole, saquinavir, telaprevir, tipranavir, telithromycin, troleandomycin, nelfinavir, clarithromycin, nefazodone, saquinavir, suboxone, and voriconazole.

In one embodiment, in the method of any one of the suitable preceding embodiments, the inhibitor of CYP3A4/5 is a moderate CYP3A4/5 inhibitor selected from a group consisting of aprepitant, ciprofloxacin, conivaptan, crizotinib, cyclosporine, diltiazem, dronedarone, erythromycin, fluconazole, fluvoxamine, imatinib, tofisopam, and verapamil.

In one embodiment, in the method of any one of the suitable preceding embodiments, the inhibitor of CYP3A4/5 is a mild CYP3A4/5 inhibitor selected from a group consisting of chlorzoxazone, cilostazol, cimetidine, clotrimazole, fosaprepitant, istradefylline, ivacaftor, lomitapide, ranitidine, ranolazine, ticagrelor.

As used herein, the terms "weak inhibitor" and "mild inhibitor" are used interchangeably.

As used herein, the terms "weak inducer" and "mild inducer" are used interchangeably.

In one embodiment, in the method of any one of the suitable preceding embodiments, the inhibitor of CYP3A4/5 is itraconazole. In one aspect, about 0.1-1000 mg of itraconazole is administered to the subject. In one aspect, itraconazole is administered in the form of an oral solution. In one aspect, about 50-500 mg of itraconazole is administered to the subject.

In one embodiment, the method of any one of the suitable preceding embodiments comprises administering about 200 mg of itraconazole to the subject. In one aspect, about 0.1-1000 mg of itraconazole is administered to the subject. In one aspect, about 50-500 mg of itraconazole is administered to the subject. In one aspect, about 200 mg of itraconazole is administered to the subject. In one aspect, about 200 mg of itraconazole is administered to the subject once daily. In one aspect, about 100 mg of itraconazole is administered to the subject. In one aspect, about 100 mg of itraconazole is administered to the subject once daily. In one aspect, itraconazole is administered in the form of an oral solution.

Diseases, Disorders and Conditions

Pyruvate kinase deficiency (PKD) is a glycolytic enzymopathy that results in life-long hemolytic anemia. In certain embodiments, the subject having PKD is a patient having at least 2 mutant alleles in PKLR gene. In certain embodiments, the subject having PKD is a patient having at least 2 mutant alleles in PKLR gene and at least one is a missense mutation. See Canu et al., Blood Cells, Molecules and Diseases 2016, 57, pp. 100-109. In certain embodiments, a subject having PKD has an Hb concentration less than or equal to 10.0 g/dL. In certain embodiments, the subject having PKD is an adult not under regular transfusion (e.g., having had no more than 4 transfusion episodes in the 12-month period up to the treatment). In certain embodiments, the subject having PKD is an adult transfusion independent (e.g., having no more than 3 units of RBCs transfused in the 12-month period prior to the treatment). In certain embodiments, the subject having PKD is an adult under regular transfusion (e.g., having had at least 4 transfusion episodes (e.g., at least 6 transfusion episodes) in the 12-month period prior to the treatment). In certain embodiments, the subject having PKD has a total number of at least 5 transfusion episodes during the subject's lifetime. In certain embodiments, the subject having PKD has a total number of at least 10 transfusion episodes during the subject's lifetime. In certain embodiments, the subject having PKD has a total number of at least 15 transfusion episodes during the subject's lifetime. In certain embodiments, the subject having PKD has a total number of at least 20 transfusion episodes during the subject's lifetime. In certain embodiments, the subject having PKD has a total number of at least 25 transfusion episodes during the subject's lifetime. In certain embodiments, the subject having PKD has a total number of at least 30 transfusion episodes during the subject's lifetime. In certain embodiments, the subject having PKD has a total number of at least 40 transfusion episodes during the subject's lifetime. In certain embodiments, the subject having PKD has a total number of at least 50 transfusion episodes during the subject's lifetime. In certain embodiments, the subject having PKD has a total number of at least 60 transfusion episodes during the subject's lifetime. In certain embodiments, the subject having PKD has a total number of at least 70 transfusion episodes during the subject's lifetime. In certain embodiments, the subject having PKD is not homozygous for the R479H mutation or does not have 2 non-missense mutations in the PKLR gene. In certain embodiments, the subject having PKD, under regular transfusion, has hemoglobin (Hb) ≤12.0 g/dL (if male) or ≤11.0 g/dL (if female), prior to the treatment. In certain embodiments, the subject having PKD, under regular transfusion, has transfusion occurring on average less than or equal to once every three weeks. In certain embodiments, the subject having PKD has received at least 0.8 mg (e.g., at least 1.0 mg)folic acid daily (e.g., for at least 21 days) prior to the treatment. In certain embodiments, the subject with PKD under regular transfusion achieves a reduction in transfusion burden (e.g., at least 33% reduction in the number of RBC units transfused) during the 5 weeks, 10 weeks, 15 weeks, 20 weeks, or 24 weeks, 28 weeks, or 32 weeks of treatment. In certain embodiments, the subject having PKD, not under regular transfusion (having had no more than 4 transfusion episodes in the 12-month period prior to the treatment and/or no transfusion in the 3 months prior to the treatment), has hemoglobin (Hb) ≤10.0 g/dL regardless of gender prior to the treatment. In certain embodiments, the subject having PKD has undergone splenectomy. In certain embodiment, the subject having PKD is a child 18 years old or younger. In certain embodiments, the child is transfusion dependent.

Exemplified conditions related to PKD include, but are not limited to, anemias, cholecystolithiasis, gallstones, tachycardia, hemochromatosis, icteric sclera, splenomegaly, leg ulcers, jaundice, fatigue, and shortness of breath. As described herein, PKD is a deficiency of PKR. In certain embodiments, the deficiency of PKR is associated with a PKR mutation.

In certain embodiments, the subject with PKD achieves a hemoglobin response of at least 1.0 g/dL increase in Hb concentration after the treatment compared to the baseline of prior to the treatment. In certain embodiments, the subject with PKD achieves a hemoglobin response of at least 1.5 g/dL increase in Hb concentration from baseline prior to the treatment. In certain embodiments, the subject with PKD achieves a hemoglobin response of at least 2.0 g/dL increase in Hb concentration from baseline prior to the treatment.

In an embodiment, the mutant PKR is selected from the group consisting of A31V, A36G, G37Q, R40W, R40Q, L73P, S80P, P82H, R86P, I90N, T93I, G95R, M107T, G111R, A115P, S120F, H121Q, S130P, S130Y, V134D, R135D, A137T, G143S, I153T, A154T, L155P, G159V, R163C, R163L, T164N, G165V, L167M, G169G, E172Q, W201R, I219T, A221Y, D221N, G222A, I224T, G232C, N253D, G263R, G263W, E266K, V269F, L272V, L272P, G275R, G275R, E277K, V280G, D281N, F287V, F287L, V288L, D293N, D293V, A295I, A295V, I310N, I314T, E315K, N316K, V320L, V320M, S330R, D331N, D331G, D331E, G332S, V335M, A336S, R337W, R337P, R337Q, D339N, D339Q, G341A, G341D, I342F, K348N, A352D, I357T, G358R, G358E, R359C, R359H, C360Y, N361D, G364D, K365M, V368F, T371I, L374P, S376I, T384M, R385W, R385K, E387G, D390N, A392T, N393D, N393S, N393K, A394S, A394D, A394V, V395L, D397V, G398A, M403I, G406R, E407K, E407G, T408P, T408A, T408I, K410E, G411S, G411A, Q421K, A423A, A423A, R426W, R426Q, E427A, E427N, A431T, R449C, I457V, G458D, A459V, V460M, A468V, A468G, A470D, T477A, R479C, R479H, S485F, R486W, R486L, R488Q, R490W, I494T, A495T, A495V, R498C, R498H, A503V, R504L, Q505E, V506I, R510Q, G511R, G511E, R518S, R531C, R532W, R532Q, E538D, G540R, D550V, V552M, G557A, R559G, R559P, N566K, M568V, R569Q, R569L, Q58X, E174X, W201X, E241X, R270X, E440X, R486X, Q501X, L508X, R510X, E538X, R559X. These mutations are described in Canu et.al., Blood Cells, Molecules and Diseases 2016, 57, pp. 100-109. In an embodiment, the mutant PKR is selected from G332S, G364D, T384M, K410E, R479H, R479K, R486W, R532W, R510Q, and R490W. In certain embodiments, the mutant PKR is selected from A468V, A495V, I90N, T408I, and Q421K, and R498H. In certain embodiments, the mutant PKR is R532W, K410E, or R510Q. In certain embodiments, the mutant PKR is R510Q, R486W, or R479H.

In other aspects, provided are methods of treating a disease selected from hemolytic anemia, hereditary spherocytosis, hereditary elliptocytosis, abetalipoproteinemia, Bassen-Kornzweig syndrome, and paroxysmal nocturnal hemoglobinuria in a subject in need thereof, comprising administering to the subject an effective amount of mitapivat or a pharmaceutically acceptable salt thereof, in combination with or in the absence of an effective amount of a secondary drug (e.g., a CYP3A4/5 inducer or a CYP3A4/5 inhibitor). Also provided is mitapivat or a pharmaceutically acceptable salt thereof, in combination with or in the absence of an effective amount of a secondary drug (e.g., a CYP3A4/5 inducer or a CYP3A4/5 inhibitor), for use in treating disease selected from hemolytic anemia, hereditary spherocytosis, hereditary elliptocytosis, abetalipoproteinemia, Bassen-Kornzweig syndrome, and paroxysmal nocturnal hemoglobinuria in a subject. Further provided is the use of mitapivat or a pharmaceutically acceptable salt thereof, in combination with or in the absence of an effective amount of a secondary drug (e.g., a CYP3A4/5 inducer or a CYP3A4/5 inhibitor), in the manufacture of a medicament for treating a disease selected from hemolytic anemia, hereditary spherocytosis, hereditary elliptocytosis, abetalipoproteinemia, Bassen-Kornzweig syndrome, and paroxysmal nocturnal hemoglobinuria in a subject in need thereof. In one aspect, the disease to be treated is hemolytic anemia.

Thalassemia is an inherited blood disorder in which the normal ratio of α- to β-globin production is disrupted due to a disease-causing variant in 1 or more of the globin genes. In certain embodiments, Alpha-globin aggregates (as found in β-thalassemia) readily precipitate, which disrupts the red blood cell (RBC) membrane and results in oxidative stress. In certain embodiments, Beta-globin tetramers (Hb H, found in a-thalassemia) are generally more soluble, but are still unstable and can form precipitates. The imbalance of the globin chain synthesis can lead to a net reduction in Hb concentrations and has dramatic effects on the survival of RBC precursors, ultimately resulting in their premature destruction in the bone marrow and in extramedullary sites (Cappellini et al., 2014). In certain embodiments, the disorder results in large numbers of red blood cells being destroyed, which leads to anemia. In certain embodiments, the thalassemia is alpha thalassemia. In certain embodiments, the thalassemia is beta thalassemia. In other embodiments, the thalassemia is non-transfusion-dependent thalassemia. In other embodiments, the thalassemia is beta thalassemia intermedia. In other embodiments, the thalassemia is Hb E beta thalassemia. In other embodiments, the thalassemia is beta thalassemia with mutations of 1 or more alfa genes.

In certain embodiments, the subject is an adult subject with thalassemia. In certain embodiments, the subject has thalassemia such as β-thalassemia intermedia, Hb E β-thalassemia, α-thalassemia (Hb H disease), or β-thalassemia with mutations of 1 or more α genes. In certain embodiments, the subject has non-transfusion-dependent thalassemia. In certain embodiments, the subject has non-transfusion-dependent alpha thalassemia. In certain embodiments, the subject has beta-thalassemia or non-transfusion-dependent beta-thalassemia. In certain embodiments, the subject is an adult male subject with thalassemia such as beta-thalassemia or non-transfusion-dependent thalassemia. In certain embodiments, the subject is a female subject with thalassemia such as beta-thalassemia or non-transfusion-dependent thalassemia. In certain embodiments, the subject is an adult female subject with thalassemia such as beta-thalassemia or non-transfusion-dependent thalassemia. In certain embodiments, the subject has a hemoglobin concentration of less than or equal to 6.0 g/dL. In certain embodiments, the subject has a hemoglobin concentration of less than or equal to 7.0 g/dL. In certain embodiments, the subject has a hemoglobin concentration of less than or equal to 8.0 g/dL. In certain embodiments, the subject has a hemoglobin concentration of less than or equal to 9.0 g/dL. In certain aspects, the subject having non-transfusion-dependent thalassemia does not have a known history (e.g., has been diagnosed in the past) of Hb S or Hb C forms of thalassemia. In certain embodiments, the term "non-transfusion dependent" thalassemia refers to subjects with thalassemia having no more than 4 (e.g., five) units of RBCs transfused during a 24-week period up to the first day of administration of mitapivat and/or no RBC transfusions in the 8 weeks prior to the first day of administration of mitapivat. In certain embodiment, the subject is an adult over 18 years old. In certain embodiment, the subject is a child 18 years old or younger.

As used herein, sickle cell disease (SCD), Hemoglobin SS disease, and sickle cell anemia are used interchangeably. Sickle cell disease (SCD) is an inherited blood disorder caused by the presence of sickle hemoglobin (HbS). In certain embodiments, subjects with SCD have abnormal hemoglobin, called hemoglobin S or sickle hemoglobin, in their red blood cells. In certain embodiments, people having SCD have at least one abnormal gene causing the body to make hemoglobin S. In certain embodiments, people having SCD have two hemoglobin S genes, Hemoglobin SS.

In other aspects, provided herein are methods for treating anemia in a subject in need thereof comprising administering to the subject an effective amount of mitapivat or a pharmaceutically acceptable salt thereof, in combination with or in the absence of an effective amount of a secondary drug (e.g., a CYP3A4/5 inducer or a CYP3A4/5 inhibitor). Also provided is mitapivat or a pharmaceutically acceptable salt thereof, in combination with or in the absence of an effective amount of a secondary drug (e.g., a CYP3A4/5 inducer or a CYP3A4/5 inhibitor), for use in treating anemia in a subject in need thereof. Further provided is the use of mitapivat or a pharmaceutically acceptable salt thereof, in combination with or in the absence of an effective amount of a secondary drug (e.g., a CYP3A4/5 inducer or a CYP3A4/5 inhibitor), in the manufacture of a medicament for treating anemia. In one aspect, the anemia to be treated is dyserythropoietic anemia.

In certain embodiments, the anemia is a dyserythropoietic anemia such as congenital dyserythropoietic anemia type I, II, III, or IV. In certain embodiments, the anemia is hemolytic anemia. In certain embodiments, the hemolytic anemia is a congenital and/or hereditary form of hemolytic anemia such as PKD, sickle cell disease, thalassemias (e.g., alpha or beta or non-transfusion-dependent thalassemia), hereditary spherocytosis, hereditary elliptocytosis), paroxysmal nocturnal hemoglobinuria, abeta-liproteinemia (Bassen-Kornzweig syndrome). In certain embodiments, the hemolytic anemia is acquired hemolytic anemia such as autoimmune hemolytic anemia, drug-induced hemolytic anemia. In certain embodiments, the hemolytic anemia is anemia as part of a multi-system disease, such as the anemia of Congenital Erythropoietic Purpura, Fanconi, Diamond-Blackfan.

As used herein, the term "anemia" refers to a deficiency of red blood cells (RBCs) and/or hemoglobin. As used herein, anemia includes all types of clinical anemia, for example (but not limited to): microcytic anemia, iron deficiency anemia, hemoglobinopathies, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle cell disease, warm autoimmune hemolytic anemia, cold agglutinin hemolytic anemia, osteopetrosis, thalassemia, and myelodysplastic syndrome.

In certain embodiments, anemia can be diagnosed on a complete blood count. In certain embodiments, anemia can be diagnosed based on the measurement of one or more markers of hemolysis (e.g., RBC count, hemoglobin, reticulocytes, schistocytes, lactate Dehydrogenase (LDH), haptoglobin, bilirubin, and ferritin) and/or hemosiderinuria mean corpuscular volume (MCV) and/or red cell distribution width (RDW). In the context of the present invention, anemia is present if an individual has a hemoglobin (Hb) less than the desired level, for example, the Hb concentration of less than 14 g/dL, more preferably of less than 13 g/dL, more preferably of less than 12 g/dL, more preferably of less than 11 g/dL, or most preferably of less than 10 g/dL.

In certain embodiments, provided herein is a method of increasing the amount of hemoglobin in a subject by administering an effective amount of mitapivat or a pharmaceutically acceptable salt thereof, in combination with or in the absence of an effective amount of a secondary drug (e.g., a CYP3A4/5 inducer or a CYP3A4/5 inhibitor). In certain embodiments, also provided herein is a method of increasing the amount of hemoglobin in a subject having thalassemia comprising administering to the subject an effective amount of mitapivat or a pharmaceutically acceptable salt thereof, in combination with or in the absence of an effective amount of a secondary drug (e.g., a CYP3A4/5 inducer or a CYP3A4/5 inhibitor). Further provided is a method of increasing the amount of hemoglobin in subjects having non-transfusion-dependent thalassemia comprising administering an effective amount of mitapivat or a pharmaceutically acceptable salt thereof, in combination with or in the absence of an effective amount of a secondary drug (e.g., a CYP3A4/5 inducer or a CYP3A4/5 inhibitor) to the subject. In certain embodiments, the provided methods increase hemoglobin concentration in the subject. In certain embodiments, the provided methods increase Hb concentration to a desired level, for example, above 10 g/dL, more preferably above 11 g/dL, more preferably above 12 g/dL, more preferably above 13 g/dL, or most preferably above 14 g/dL. In certain embodiments, the provided methods increase Hb concentration by at least about 0.5 g/dL. In certain embodiments, the provided methods increase Hb concentration by at least about 1.0 g/dL. In certain embodiments, the provided methods increase Hb concentration by at least about 1.5 g/dL. In certain embodiments, the provided methods increase Hb concentration by at least about 2.0 g/dL. In certain embodiments, the provided methods increase Hb concentration by at least about 2.5 g/dL. In certain embodiments, the provided methods increase Hb concentration by at least about 3.0 g/dL. In certain embodiments, the provided methods increase Hb concentration by at least about 3.5 g/dL. In certain embodiments, the provided methods increase Hb concentration by at least about 4.0 g/dL. In certain embodiments, the provided methods increase Hb concentration by at least about 4.5 g/dL. In certain embodiments, the provided methods increase Hb concentration by at least about 5.0 g/dL. In certain embodiments, the provided methods increase Hb concentration by at least about 5.5 g/dL. In certain embodiments, the provided methods increase Hb concentration by at least about 6.0 g/dL. In certain embodiments, the increase in Hb concentration is determined from baseline at one or more assessment between week 1 and week 20 (e.g., between week 2 and week 15, between week 3 and week 15, and between week 4 and week 12) of treatment with an effective amount of mitapivat or a pharmaceutically acceptable salt thereof, in combination with or in the absence of an effective amount of a secondary drug (e.g., a CYP3A4/5 inducer or a CYP3A4/5 inhibitor). In certain embodiments, the provided methods increase Hb concentration as described above in female subjects having thalassemia (e.g., beta-thalassemia or non-transfusion-dependent thalassemia). In certain embodiments, the provided methods increase Hb concentration from baseline to about 12 g/dL in female subjects having thalassemia (e.g., beta-thalassemia or non-transfusion-dependent thalassemia). In certain embodiments, the provided methods increase Hb concentration as described above in male subjects having thalassemia (e.g., beta-thalassemia or non-transfusion-dependent thalassemia). In certain embodiments, the provided methods increase Hb concentration from baseline to about 13 g/dL in male subjects having thalassemia (e.g., beta-thalassemia or non-transfusion-dependent thalassemia).

In some aspects, provided herein are methods for treating hemolytic anemia in a subject in need thereof comprising administering to the subject an effective amount of mitapivat or a pharmaceutically acceptable salt thereof, in combination with or in the absence of an effective amount of a secondary drug (e.g., a CYP3A4/5 inducer or a CYP3A4/5 inhibitor). Also provided is mitapivat or a pharmaceutically acceptable salt thereof, in combination with or in the absence of an effective amount of a secondary drug (e.g., a CYP3A4/5 inducer or a CYP3A4/5 inhibitor), for use in treating hemolytic anemia in a subject in need thereof. Further provided is the use of mitapivat or a pharmaceutically acceptable salt thereof, in combination with or in the absence of an effective amount of a secondary drug (e.g., a CYP3A4/5 inducer or a CYP3A4/5 inhibitor), in the manufacture of a medicament for treating hemolytic anemia. In one aspect, the hemolytic anemia to be treated is hereditary and/or congenital hemolytic anemia, acquired hemolytic anemia, or anemia as part of a multi-system disease.

In some aspects, provided herein are methods for activating wild-type or mutant PKR in red blood cells in a subject in need thereof comprising administering to the subject an effective amount of mitapivat or a pharmaceutically acceptable salt thereof, in combination with or in the absence of an effective amount of a secondary drug (e.g., a CYP3A4/5 inducer or a CYP3A4/5 inhibitor). Also provided is mitapivat or a pharmaceutically acceptable salt thereof, in combination with or in the absence of an effective amount of a secondary drug (e.g., a CYP3A4/5 inducer or a CYP3A4/5 inhibitor), for use in activating wild-type or mutant PKR in red blood cells in a subject in need thereof. Further provided is the use of mitapivat or a pharmaceutically acceptable salt thereof, in combination with or in the absence of an effective amount of a secondary drug (e.g., a CYP3A4/5 inducer or a CYP3A4/5 inhibitor), in the manufacture of a medicament for activating wild-type or mutant PKR in red blood cells.

Mitapivat is an activator of PKR mutants having lower activities compared to the wild type, thus are useful for methods of the present disclosure. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al., JBC 2002. Some examples of the mutants that are activated by the compounds described herein include G332S, G364D, T384M, R479H, R479K, R486W, R532W, R510Q, and R490W. Without being bound by theory, in certain embodiments, mitapivat affects the activities of PKR mutants by activating FBP non-responsive PKR mutants, restoring thermostability to mutants with decreased stability, or restoring catalytic efficiency to impaired mutants.

In certain embodiments, mitapivat increases the affinity of PKR to phosphoenolpyruvate (PEP). In certain embodiments, mitapivat restores the ability of RBCs to cover PEP and ADP to pyruvate and ATP.

In certain embodiments, provided herein are methods of reducing transfusion frequency of a subject with PKD comprising administering to the subject mitapivat or a pharmaceutically acceptable salt thereof, in combination with or in the absence of an effective amount of a secondary drug (e.g., a CYP3A4/5 inducer or a CYP3A4/5 inhibitor). In certain embodiments, the transfusion frequency is reduced by at least 5% in the number of RBC units transfused over at least 15 weeks. In certain embodiments, the transfusion frequency is reduced by at least 10% in the number of RBC units transfused over at least 15 weeks. In certain embodiments, the transfusion frequency is reduced by at least 15% in the number of RBC units transfused over at least 15 weeks. In certain embodiments, the transfusion frequency is reduced by at least 20% in the number of RBC units transfused over at least 15 weeks. In certain embodiments, the transfusion frequency is reduced by at least 25% in the number of RBC units transfused over at least 15 weeks. In certain embodiments, the transfusion frequency is reduced by at least 30% in the number of RBC units transfused over at least 15 weeks. In certain embodiments, the transfusion frequency is reduced by at least 35% in the number of RBC units transfused over at least 15 weeks. In certain embodiments, the transfusion frequency is reduced by at least 40% in the number of RBC units transfused over at least 20 weeks. In certain embodiments, the transfusion frequency is reduced by at least 5% in the number of RBC units transfused over at least 20 weeks. In certain embodiments, the transfusion frequency is reduced by at least 10% in the number of RBC units transfused over at least 20 weeks. In certain embodiments, the transfusion frequency is reduced by at least 15% in the number of RBC units transfused over at least 20 weeks. In certain embodiments, the transfusion frequency is reduced by at least 20% in the number of RBC units transfused over at least 20 weeks. In certain embodiments, the transfusion frequency is reduced by at least 25% in the number of RBC units transfused over at least 20 weeks. In certain embodiments, the transfusion frequency is reduced by at least 30% in the number of RBC units transfused over at least 20 weeks. In certain embodiments, the transfusion frequency is reduced by at least 35% in the number of RBC units transfused over at least 20 weeks. In certain embodiments, the transfusion frequency is reduced by at least 40% in the number of RBC units transfused over at least 20 weeks.

In some aspects, provided herein are methods of evaluating the efficacy of mitapivat therapy (monotherapy or concomitant medications with a CYP3A4/5 inducer or a CYP3A4/5 inhibitor) in a subject, the method comprising: administering to the subject mitapivat or a pharmaceutically acceptable salt thereof, in combination with or in the absence of an effective amount of a secondary drug (e.g., a CYP3A4/5 inducer or a CYP3A4/5 inhibitor); and acquiring a value for the level of mitapivat, the level of 2,3-diphosphoglycerate (2,3-DPG), the level of adenosine triphosphate (ATP), or the activity of PKR in the subject, to thereby evaluate the efficacy of the mitapivat therapy. In some aspects, the value for the level is acquired by analyzing the plasma concentration of mitapivat and optionally, the metabolite known to be formed by CYP3A4/5. In some aspects, the level of 2,3-DPG is acquired by analyzing the blood concentration of 2,3-DPG. In some aspects, the level of ATP is acquired by analyzing the blood concentration of ATP. In some aspects, the activity of PKR is acquired by analyzing the blood concentration of a $^{13}$C-label in the blood. In some aspects, the analysis is performed by sample analysis of bodily fluid. In some aspects, the bodily fluid is blood. In some aspects, the analysis is performed by mass spectroscopy. In some aspects, the analysis is performed by LC-MS.

In some aspects, provided herein are methods of treating a subject, the method comprising: administering to the subject an effective amount of mitapivat or a pharmaceutically acceptable salt thereof, in combination with or in the absence of an effective amount of a secondary drug (e.g., a CYP3A4/5 inducer or a CYP3A4/5 inhibitor); and acquiring a value for the level of mitapivat and optionally its metabolite known to be formed by CYP3A4/5, the level of 2,3-diphosphoglycerate (2,3-DPG), the level of adenosine triphosphate (ATP), or the activity of PKR in the subject, to thereby treat the subject.

EXEMPLIFICATIONS

As depicted in the Examples below, the drug-drug interactions between mitapivat sulfate and a CYP3A4/5 inducer (e.g., rifampin) or a CYP3A4/5 inhibitor (e.g., itraconazole) are studied. Mitapivat can be synthesized using the procedures described in International Patent Application Publication Nos. WO 2011/002817 and WO 2016/201227.

Example 1: Mitapivat sulfate is primarily metabolized by CYP3A4

CYP-enzyme phenotyping using human liver microsomes and recombinant CYP enzymes revealed that mitapivat sulfate was primarily metabolized by CYP3A4/5 (>90%), with minor contributions from CYP2C9, CYP2C8, and CYP1A2. There was evidence of metabolism-dependent inhibition of CYP2C19 (largely reversible) and CYP3A4 (largely irreversible). Mitapivat sulfate was found to be a substrate and inhibitor for P-gp but not for breast cancer resistance protein (BCRP) and was found to be a potential inducer of human CYP2B6 and CYP3A4. Mitapivat sulfate appeared to be a mild inhibitor of CYP2C8, CYP2C9, xYP2C19, CYP2D6, and CYP3A4/5 enzymes (testosterone 6β-hydroxylation), bile salts export pump (BSEP), organic anion transporting polypeptide (OATP)1B1, organic anion transporter (OAT)3, and organic cation transporter (OCT)2, and of uridine-5'-diphospho-glucuronosyltransferase (UGT) 1A3, 1A4, and 1A9. Mitapivat sulfate does not appear to be an inhibitor of multidrug resistance-associated protein (MRP)2, MRP3, OATP1B3, and OAT1. The metabolite was found to be a mild inhibitor of CYP2C9 and CYP2C19 and was not an inhibitor of P-gp or BCRP under tested concentrations.

Example 2: Drug-drug Interaction (DDI) Studies of Mitapivat Sulfate and a CYP3A4 Inducer or a CYP3A4 Inhibitor Twenty-eight (28) healthy, adult male and female (non-childbearing potential) subjects were enrolled in the study in total; 14 subjects in each study part (Parts 1 and 2). A minimum of 8 female subjects were enrolled in the study (i.e., a minimum of 4 female subjects per study part). Each subject participated in either Part 1 or Part 2, but not both.

Part 1

On Day 1 of Treatment Period 1, a single oral dose of 20 mg mitapivat sulfate was administered. Serial blood samples for plasma assay of mitapivat concentrations and its CYP3A4 metabolite, referred to herein as the "Metabolite" (structure below),

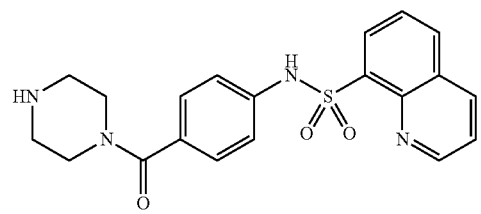 [SMILES: O=C(c1ccc(NS(=O)(=O)c2cccc3cccnc23)cc1)N1CCNCC1]

were collected from predose to 120 hours following administration of mitapivat sulfate. In Treatment Period 2, an oral dose of 200 mg itraconazole was administered once daily (QD) for 9 consecutive days (Day 1 through Day 9 of Treatment Period 2) with a single oral dose of 20 mg mitapivat sulfate coadministered on Day 5. Serial blood samples for plasma assay of mitapivat and the Metabolite concentrations were collected from predose to 120 hours following coadministration of mitapivat sulfate and itraconazole on Day 5.

In Treatment Period 1, mitapivat sulfate was administered orally with approximately 240 mL of water. In Treatment Period 2, on Days 1 to 4, itraconazole was administered alone immediately followed by approximately 220 mL of water, and on Day 5, itraconazole was administered first (no water) and was immediately followed by mitapivat sulfate administration with approximately 220 mL of water. Study drugs (mitapivat sulfate and itraconazole) were administered following an overnight fast of at least 10 hours on Day 1 of Treatment Period 1 (mitapivat sulfate only) and Day 5 of Treatment Period 2 (mitapivat sulfate and itraconazole), and subjects remained fasted for 4 hours after dosing. On all other dosing days, itraconazole was administered following a predose fast of at least 4 hours and subjects remained fasted for at least 2 hours after dosing.

Part 2

On Day 1 of Treatment Period 1, a single oral dose of 50 mg mitapivat sulfate was administered. Serial blood samples for plasma assay of mitapivat and the Metabolite concentrations were collected from predose to 120 hours following administration of mitapivat sulfate. In Treatment Period 2, an oral dose of 600 mg rifampin was administered QD for 12 consecutive days (Day 1 through Day 12 of Treatment Period 2) with a single oral dose of 50 mg mitapivat sulfate coadministered on Day 8. Serial blood samples for plasma assay of mitapivat sulfate and the Metabolite concentrations were collected from predose to 120 hours following coadministration of mitapivat and rifampin on Day 8.

In Part 2, study drugs were administered with approximately 240 mL of water on all dosing days including the coadministration of mitapivat sulfate and rifampin on Day 8 of Treatment Period 2. Mitapivat sulfate and rifampin was administered following an overnight fast of at least 10 hours on Day 1 of Treatment Period 1 (mitapivat sulfate only) and Day 8 of Treatment Period 2 (both mitapivat sulfate and rifampin) and subjects remained fasted for 4 hours after dosing. On all other dosing days, rifampin was administered following a predose fast of at least 4 hours and subjects remained fasted for at least 2 hours after dosing. There was a washout period of 7 days between the mitapivat sulfate dose in Treatment Period 1 and the first itraconazole (Part 1) or rifampin (Part 2) dose in Treatment Period 2. All study drugs were consumed within 5 minutes for both Part 1 and Part 2.

Test and Reference Products, Dose, Duration and Mode of Administration

Part 1

Mitapivat sulfate (20 mg tablets) administered along with Itraconazole (also referred to as Sporanox®, 10 mg/mL oral solution, is considered as the test arm in this study. Mitapivat sulfate administered alone is considered as the reference arm in this study. In Period 1, a single oral dose of 20 mg mitapivat sulfate was administered orally with approximately 240 mL of water. In Period 2, on Day 5 (coadministration of itraconazole and mitapivat sulfate), 200 mg itraconazole (20 mL of 10 mg/mL oral solution) was administered first (no water) and was immediately followed by 20 mg mitapivat sulfate (1×20 mg tablet) administration with approximately 220 mL of water. On all other dosing days, itraconazole was administered alone immediately followed by approximately 220 mL of water. Each subject received 2 doses of mitapivat sulfate and 9 doses of itraconazole in Part 1.

Part 2

Mitapivat sulfate (50 mg tablets) administered along with Rifampin (also referred to as Rifadin®, 300 mg capsules) is considered as the test arm in this study. Mitapivat sulfate (50 mg tablets) administered alone is considered as the reference arm in this study.

In Period 1, a single oral dose of 50 mg mitapivat sulfate was administered orally. In Period 2, subjects were administered 600 mg rifampin (2×300 mg capsules) QD on Day 1 to Day 12 inclusive, with 50 mg mitapivat sulfate (1×50 mg tablet) coadministered on Day 8. Study drugs were administered with approximately 240 mL of water on all dosing days including the coadministration of mitapivat sulfate and rifampin on Day 8 of Period 2.

Each subject received 2 doses of mitapivat sulfate and 12 doses of rifampin in Part 2.

Duration of Treatment:

The total duration of participation including the screening period for each subject was approximately 49 to 62 days for Part 1 and approximately 61 or 63 days in Part 2 of the study.

In each study part, Treatment Period 1 was approximately 6 days and Treatment Period 2 was approximately 12 days; a washout phase was 7 days between both treatment periods in each study part.

Criteria for Evaluation of Pharmacokinetics

In Parts 1 and 2, for mitapivat and the Metabolite, blood samples were obtained for all subjects to determine the plasma concentrations of mitapivat, and the Metabolite, before mitapivat sulfate dosing (0 hour) on Day 1 of Period 1 (Parts 1 and 2) and Day 5 (Part 1) or Day 8 (Part 2) of Period 2 at 0.5, 1, 1.5, 2, 3, 4, 5, 6, 8, 12, 16, 24, 48, 72, 96, and 120 hours postdose. Plasma concentrations of mitapivat and the Metabolite were determined using methods validated with respect to accuracy, precision, linearity, sensitivity, and specificity, with a lower limit of quantitation (LLOQ) of 0.5 ng/mL for both analytes. A noncompartmental PK approach was used to analyze individual plasma mitapivat and the Metabolite concentration time data (using Phoenix® WinNonlin® Version 7.0). The following PK parameters were calculated: $AUC_{0-t}$, $AUC_{0-inf}$, $AUC_{0-24}$, $AUC_{\%extrap}$, Cmax, CL/F (mitapivat only), Tlast, Tmax, t½, and Vz/F (mitapivat only).

Statistical Methods for Pharmacokinetics

The plasma concentrations of mitapivat and the Metabolite were listed and summarized by treatment and collection time for all subjects in the PK Population. Plasma concentrations were presented with the same level of precision as received from the bioanalytical laboratory including sample size (n), arithmetic mean (Mean), standard deviation (SD), coefficient of variation (CV%), standard error of the mean (SEM), minimum, maximum, and median. Concentrations from excluded subjects were included in the plasma concentration tables, but were excluded from the summary statistics and noted as such in the tables. All BLQ values were presented as "BLQ" in the plasma concentration table listings and footnoted accordingly.

PK parameters were presented with a minimum of 3 significant figures. PK parameters were listed by subject, tabulated by treatment, and summarized using descriptive statistics (n, mean, SD, CV%, SEM, minimum, median, maximum, geometric mean (Geom. Mean) and geometric mean coefficient of variation (Geom. CV%). Time-based parameters (i.e., Tmax and t½) and treatment:reference AUC and Cmax ratios were presented to 2 decimals. Excluded subjects were included in the PK parameter table listings, but were excluded from the summary statistics and noted as such in the tables.

To evaluate the effect of itraconazole and rifampin on mitapivat and the Metabolite (primary objective), plasma mitapivat and the Metabolite PK parameters (Cmax, $AUC_{0-t}$, and $AUC_{0-inf}$) were natural log (ln) transformed before analysis. The ln-transformed value of the PK parameters was analyzed using a linear mixed effect model for each study part separately with treatment as a fixed effect and subject as a random effect. The linear mixed effect model included treatment as a fixed effect and subject as a random effect. The inferential results (least-squares means [LSMs], difference between LSMs, and 90% confidence intervals [CIs] of the difference) were back transformed to the original scale. Geometric LSMs, geometric mean ratios (GMRs), and 90% CIs were presented. The GMR of the LSMs were calculated from the back-transformed difference between the treatment LSMs. The GMRs were expressed as a percentage relative to mitapivat sulfate given alone for both Part 1 and Part 2. The 90% CIs for the ratios were derived by back-transformation of the CIs obtained for the difference between the treatment LSMs. The CIs were expressed as a percentage relative to mitapivat sulfate given alone for both Part 1 and Part 2.

The median differences in Tmax for evaluation of the effect of itraconazole and rifampin on mitapivat and the Metabolite along with the range of the difference were calculated using the non parametric Wilcoxon Signed Rank test, and the p-value was presented. Note that Tmax was not ln-transformed for these analyses.

Pharmacokinetic Results

Part 1

Figure 2:
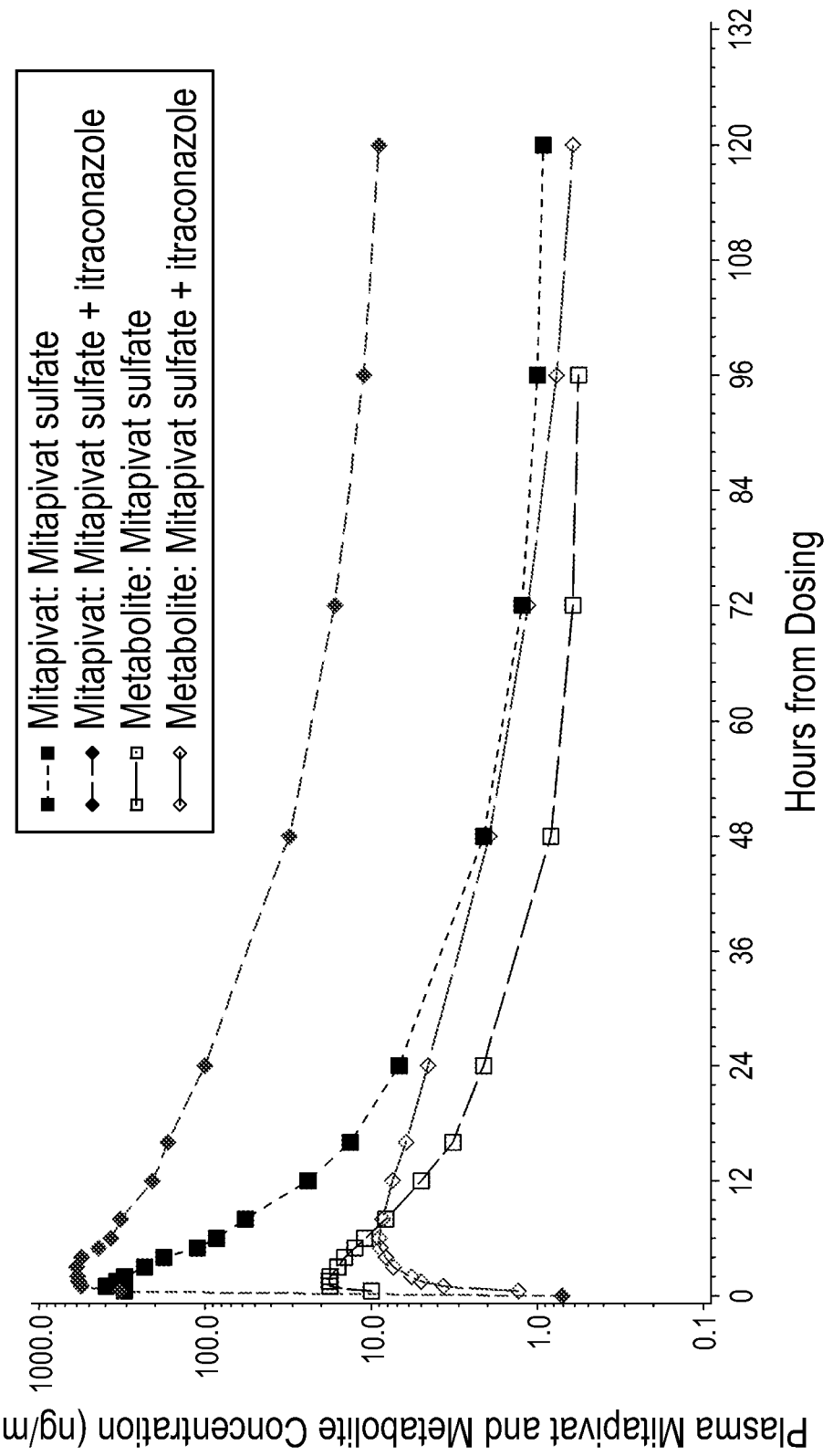
FIG. 2 is a graph showing Arithmetic Mean Plasma Mitapivat and Metabolite Concentration-Time Profiles following administration of 20 mg mitapivat sulfate alone (Treatment Period 1) and co-administered with multiple doses of 200 mg itraconazole (Treatment Period 2) on semi-log scale (Part 1) (see Example 2).

Mean plasma mitapivat and the Metabolite concentration-time profiles following 20 mg mitapivat sulfate administered alone (Period 1) or coadministered with multiple doses of 200 mg itraconazole (Period 2) on linear and semi-log scales are presented in FIGS. 1 and 2.

Mitapivat

Mitapivat plasma concentrations were detectable in all subjects at 0.5 hour (the first scheduled postdose sample) in both Periods 1 and 2. Mitapivat was still detectable up to the last sample time at 120 hours postdose in the majority of subjects in Period 1 and in all subjects in Period 2.

Measurable predose mitapivat concentrations were present in all but 2 subjects in Period 2 (two subjects were BLQ). As used herein, BLQ refers to below the limit of quantification. These predose concentrations were <5% of the Cmax, so PK calculations were performed.

Mitapivat concentrations exhibited a characteristic multi-compartmental pharmacokinetic profile. When coadministered with itraconazole, mitapivat concentrations rose to a higher mean peak with a delay in time to peak by approximately 2 hours compared to when the drug was administered alone. The post-peak decline of the multi-compartmental behavior was slower after coadministration with itraconazole when compared to mitapivat administered alone. Overall, higher mitapivat concentrations were experienced for a longer time period when mitapivat was coadministered with itraconazole.

The Metabolite

When mitapivat was administered alone, the Metabolite plasma concentrations were detectable in all but 1 subject at 0.5 hour. The Metabolite remained detectable all but 1 subject up to 48 hours postdose, with quantifiable the Metabolite out to 72 hours in 3 subjects and 96 hours in 1 subject. In Period 2 (coadministration with itraconazole), the Metabolite concentrations were delayed relative to administration of mitapivat alone. Concentrations were not measurable in all subjects until 1.5 hours postdose. Maximum concentrations were also reduced. However, the Metabolite residence was prolonged in the presence of itraconazole, with concentrations still detectable in all but 1 subject throughout the 120-hour sampling interval (in 1 subject the last measurable concentration was at 96 hours postdose).

The statistical comparisons of mitapivat PK parameters following 20 mg mitapivat sulfate administered alone (Period 1) or coadministered with multiple doses of 200 mg itraconazole (Period 2) PK parameters are summarized below in Table 1.

TABLE 1

Summary of Statistical Comparisons of Plasma Mitapivat Pharmacokinetic Parameters Following 20 mg Mitapivat Sulfate Co-Administered With Multiple Doses of 200 mg Itraconazole Versus Administered Alone (Part 1)

| Parameter (unit) | Mitapivat Sulfate + Itraconazole (Test) Geometric LSM | n | Mitapivat sulfate alone (Reference) Geometric LSM | n | GMR | 90% Confidence Interval | Intra-subject CV % |
|---|---|---|---|---|---|---|---|
| $AUC_{0-t}$ (ng*hr/mL) | 8860 | 14 | 1885 | 14 | 4.6998 | 4.2519-5.1949 | 15.05 |
| $AUC_{0-inf}$ (ng*hr/mL) | 9475 | 14 | 1942 | 14 | 4.8780 | 4.4154-5.3890 | 14.97 |
| $C_{max}$ (ng/mL) | 704.3 | 14 | 412.5 | 14 | 1.7074 | 1.5815-1.8433 | 11.48 |

Mitapivat sulfate alone: 20 mg mitapivat sulfate (1 × 20 mg tablet) at Hour 0 on Day 1 (Period 1)
Mitapivat sulfate + itraconazole: 200 mg itraconazole (20 mL of 10 mg/mL oral solution) QD on Days 1 to Day 9 inclusive (within ± 1 hour of dosing time on Day 1) with 20 mg mitapivat sulfate (1 × 20 mg tablet) coadministered at Hour 0 on Day 5 (Period 2)
Geometric least-squares means (LSMs) are calculated by exponentiating the LSMs from the linear mixed effect model.
Geometric Mean Ratio (GMR) = test/reference
Intra-subject CV % = 100 × (square root (exp[MSE] − 1), where MSE = Residual variance from linear mixed effect model.

The coadministration of 200 mg itraconazole with 20 mg mitapivat sulfate increased mitapivat exposure relative to when mitapivat sulfate was administered alone. The geometric mean $AUC_{0-t}$ and $AUC_{0-inf}$ ratios of mitapivat in the presence and absence of itraconazole were 4.7 and 4.9, respectively. The geometric mean Cmax ratio of mitapivat in the presence and absence of itraconazole was 1.7. The intra-subject variability was low at approximately 15% for AUCs and 11% for Cmax.

The statistical comparisons of the Metabolite PK parameters following 20 mg mitapivat sulfate administered alone (Period 1) or coadministered with multiple doses of 200 mg itraconazole (Period 2) PK parameters are summarized below in Table 2.

TABLE 2

Summary of Statistical Comparisons of Plasma Metabolite Pharmacokinetic Parameters Following 20 mg Mitapivat Sulfate Co-Administered With Multiple Doses of 200 mg Itraconazole Versus Administered Alone (Part 1)

| Parameter (unit) | Mitapivat Sulfate + Itraconazole (Test) Geometric LSM | n | Mitapivat sulfate alone (Reference) Geometric LSM | n | GMR | 90% Confidence Interval | Intra-subject CV % |
|---|---|---|---|---|---|---|---|
| $AUC_{0-t}$ (ng*hr/mL) | 300.0 | 14 | 197.1 | 14 | 1.5218 | 1.4268-1.6231 | 9.65 |

TABLE 2-continued

Summary of Statistical Comparisons of Plasma Metabolite Pharmacokinetic Parameters Following 20 mg Mitapivat Sulfate Co-Administered With Multiple Doses of 200 mg Itraconazole Versus Administered Alone (Part 1)

| Parameter (unit) | Mitapivat Sulfate + Itraconazole (Test) | | Mitapivat sulfate alone (Reference) | | | | |
|---|---|---|---|---|---|---|---|
| | Geometric LSM | n | Geometric LSM | n | GMR | 90% Confidence Interval | Intra-subject CV % |
| $AUC_{0\text{-}inf}$ (ng*hr/mL) | 338.6 | 14 | 216.2 | 14 | 1.5661 | 1.4784-1.6590 | 8.63 |
| $C_{max}$ (ng/mL) | 9.110 | 14 | 18.79 | 14 | 0.4849 | 0.4441-0.5295 | 13.20 |

Mitapivat sulfate alone: 20 mg mitapivat sulfate (1 × 20 mg tablet) at Hour 0 on Day 1 (Period 1)
Mitapivat sulfate + itraconazole: 200 mg itraconazole (20 mL of 10 mg/mL oral solution) QD on Days 1 to Day 9 inclusive (within ± 1 hour of dosing time on Day 1) with 20 mg mitapivat sulfate (1 × 20 mg tablet) coadministered at Hour 0 on Day 5 (Period 2)
Geometric least-squares means (LSMs) are calculated by exponentiating the LSMs from the linear mixed effect model.
Geometric Mean Ratio (GMR) = test/reference
Intra-subject CV % = 100 × (square root (exp[MSE] − 1), where MSE = Residual variance from linear mixed effect model.

The coadministration of 200 mg itraconazole with 20 mg mitapivat sulfate increased total Metabolite exposure relative to when mitapivat sulfate was administered alone. The geometric mean $AUC_{0\text{-}t}$ and $AUC_{0\text{-}inf}$ ratios of the Metabolite in the presence and absence of itraconazole were 1.5 and 1.6, respectively. The geometric mean Cmax ratio of the Metabolite in the presence and absence of itraconazole was 0.5. The intra-subject variability was low at approximately 9% to 10% for AUCs and 13% for Cmax.

Part 2

Figure 3:
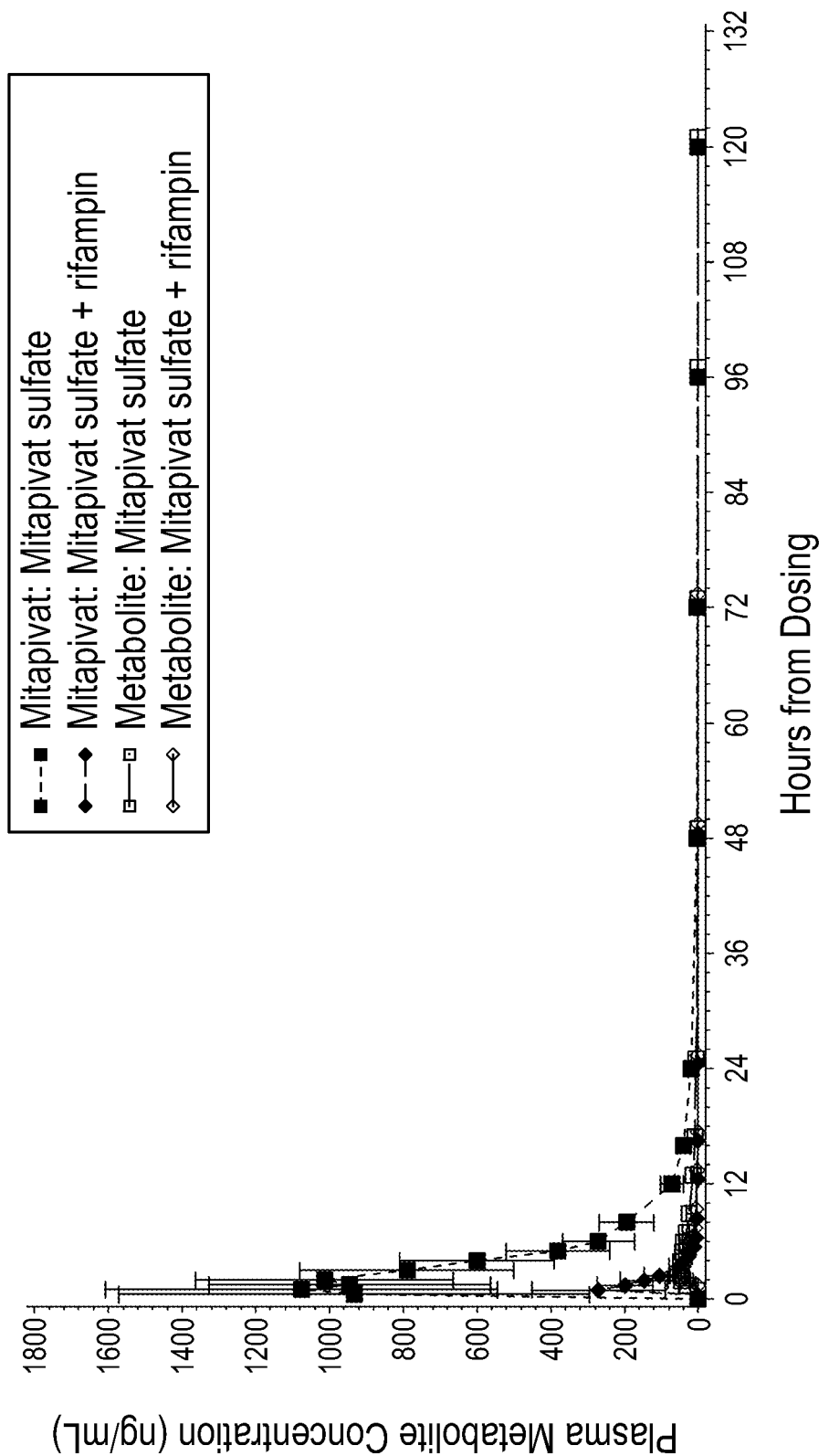
FIG. 3 is a graph showing Arithmetic Mean (SD) Plasma Mitapivat and Metabolite Concentration-Time Profiles following administration of 50 mg mitapivat sulfate alone (Treatment Period 1) and co-administered with multiple doses of 600 mg rifampin on linear scale (Treatment Period 2, Part 2, see Example 2).
Figure 4:
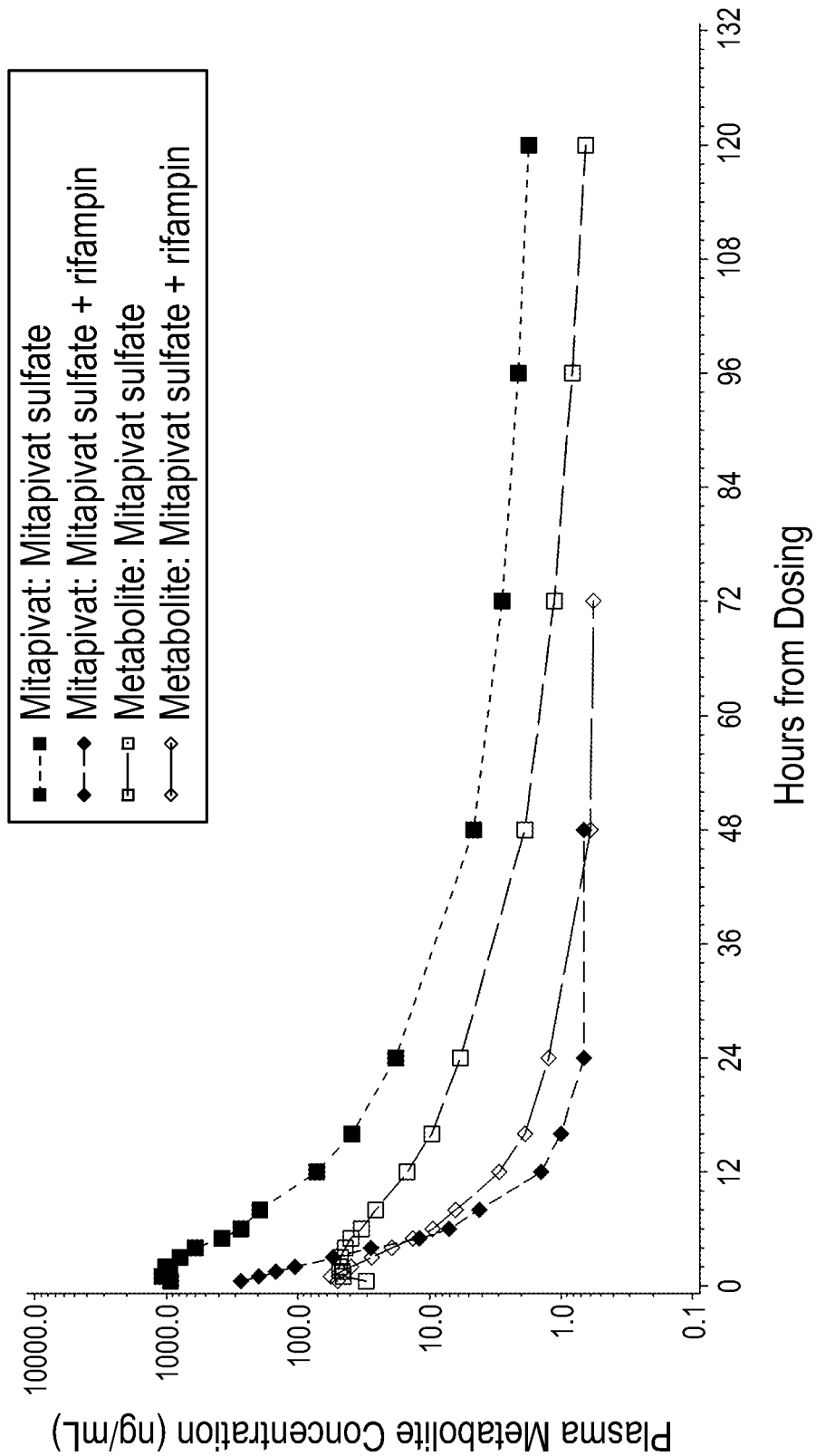
FIG. 4 is a graph showing Arithmetic Mean Plasma Mitapivat and Metabolite Concentration-Time Profiles following administration of 50 mg mitapivat sulfate alone (Treatment Period 1) and co-administered with multiple doses of 600 mg rifampin on semi-log scale (Treatment Period 2, Part 2, see Example 2)

Mean plasma mitapivat and metabolite the Metabolite concentration-time profiles following 50 mg mitapivat sulfate administered alone (Period 1) or coadministered with multiple doses of 600 mg rifampin (Period 2) on linear and semi-log scales are presented in FIGS. 3 and 4.

Mitapivat

Mitapivat plasma concentrations were detectable in all subjects at 0.5 hour (the 1st scheduled postdose sample) when given alone or with rifampin. Mitapivat was still detectable up to the last sample time at 120 hours postdose in all but 1 subject when given alone had a BLQ concentration at 120 hours). When coadministered with rifampin, detectable mitapivat concentrations were not present in any sample collections from any subject beyond 24 hours postdose (except 1 subject with detectable mitapivat at 48 hours).

Mitapivat concentrations increased to a lower and slightly earlier peak when coadministered with rifampin compared to when administered alone. The peak arithmetic mean mitapivat concentrations were observed at a nominal time of approximately 1 hour postdose for Period 1 and 0.5 hour postdose for Period 2. The mean concentrations of mitapivat then declined in a multi exponential manner for both periods; however, the post-peak initial decline in mitapivat concentrations was more rapid and to lower levels when coadministered with rifampin compared to dosing alone.

The Metabolite

The Metabolite plasma concentrations were detectable at 0.5 hour postdose in all subjects after mitapivat sulfate was given alone and in all but 1 subject (1 subject was reported as BLQ) when mitapivat sulfate was coadministered with rifampin. The Metabolite was still detectable in all but 4 subjects up to the last scheduled sampling time of 120 hours postdose when mitapivat sulfate was given alone. When mitapivat sulfate was coadministered with rifampin, the Metabolite remained detectable in all subjects up to 24 hours postdose, with quantifiable the Metabolite out to 48 hours in 6 subjects and 72 hours in 1 subject. No Metabolite concentrations were detectable in samples collected beyond 72 hours.

The peak arithmetic mean Metabolite concentrations were observed at a nominal time of approximately 2 hours postdose with mitapivat sulfate given alone and 1 hour when mitapivat sulfate was coadministered with rifampin. When mitapivat sulfate was given alone, higher mean concentrations the Metabolite were observed over the initial 1 hour postdose. Metabolite concentrations were higher when mitapivat sulfate was coadministered with rifampin beyond 1 hour. The mean concentrations of the Metabolite then declined in a multi exponential fashion for both treatments. Decline in Metabolite concentrations was more rapid when mitapivat sulfate was coadministered with rifampin.

The statistical comparisons of mitapivat PK parameters following 50 mg mitapivat sulfate administered alone (Period 1) or coadministered with multiple doses of 600 mg rifampin (Period 2) PK parameters are summarized below in Table 3.

TABLE 3

Summary of Statistical Comparisons of Plasma Mitapivat Pharmacokinetic Parameters Following 50 mg Mitapivat Sulfate Co-Administered With Multiple Doses of 600 mg Rifampin Versus Administered Alone (Part 2)

| Parameter (unit) | Mitapivat sulfate + rifampin (Test) | | Mitapivat sulfate alone (Reference) | | | | |
|---|---|---|---|---|---|---|---|
| | Geometric LSM | n | Geometric LSM | n | GMR | 90% Confidence Interval | Intra-subject CV % |
| $AUC_{0\text{-}t}$ (ng*hr/mL) | 486.4 | 14 | 5565 | 14 | 0.0874 | 0.0719-0.1062 | 29.73 |
| $AUC_{0\text{-}inf}$ (ng*hr/mL) | 496.4 | 14 | 5681 | 14 | 0.0874 | 0.0719-0.1062 | 29.84 |
| $C_{max}$ (ng/mL) | 292.4 | 14 | 1263 | 14 | 0.2316 | 0.1933-0.2773 | 27.45 |

Mitapivat sulfate alone: 50 mg mitapivat sulfate (1 × 50 mg tablet) at Hour 0 on Day 1 (Period 1)
Mitapivat sulfate + rifampin: 600 mg rifampin (2 × 300 mg capsules) QD on Day 1 to Day 12 inclusive (within ± 1 hour of dosing time on Day 1) with 50 mg mitapivat sulfate (1 × 50 mg tablet) coadministered at Hour 0 on Day 8 (Period 2)
Geometric least-squares means (LSMs) are calculated by exponentiating the LSMs from the linear mixed effect model.
Geometric Mean Ratio (GMR) = test/reference
Intra-subject CV % = 100 × (square root (exp[MSE] − 1), where MSE = Residual variance from linear mixed effect model.

The coadministration of 600 mg rifampin with 50 mg mitapivat sulfate decreased mitapivat exposure relative to when mitapivat sulfate was administered alone. The geometric mean $AUC_{0\text{-}t}$ and $AUC_{0\text{-}inf}$ ratios of mitapivat in the presence and absence of rifampin were 0.09. The geometric mean Cmax ratio of mitapivat in the presence and absence of rifampin was 0.23. The intra-subject variability was low at approximately 30% for AUCs and 27% for Cmax.

The statistical comparisons of Metabolite PK parameters following 50 mg mitapivat sulfate administered alone (Period 1) or co-administered with multiple doses of 600 mg rifampin (Period 2) PK parameters are summarized below in Table 4.

TABLE 4

Summary of Statistical Comparisons of Plasma Metabolite Pharmacokinetic Parameters Following 50 mg Mitapivat Sulfate Co-Administered With Multiple Doses of 600 mg Rifampin Versus Administered Alone (Part 2)

| Parameter (unit) | Mitapivat sulfate + rifampin (Test) Geometric LSM | n | Mitapivat sulfate alone (Reference) Geometric LSM | n | GMR | 90% Confidence Interval | Intra-subject CV % |
|---|---|---|---|---|---|---|---|
| $AUC_{0-t}$ (ng*hr/mL) | 230.5 | 14 | 623.0 | 14 | 0.3700 | 0.3316-0.4129 | 16.50 |
| $AUC_{0-inf}$ (ng*hr/mL) | 244.9 | 14 | 662.6 | 14 | 0.3696 | 0.3321-0.4113 | 16.08 |
| $C_{max}$ (ng/mL) | 64.47 | 14 | 53.80 | 14 | 1.1983 | 1.0642-1.3492 | 17.86 |

Mitapivat sulfate alone: 50 mg mitapivat sulfate (1 × 50 mg tablet) at Hour 0 on Day 1 (Period 1)
Mitapivat sulfate + rifampin: 600 mg rifampin (2 × 300 mg capsules) QD on Day 1 to Day 12 inclusive (within ± 1 hour of dosing time on Day 1) with 50 mg mitapivat sulfate (1 × 50 mg tablet) coadministered at Hour 0 on Day 8 (Period 2)
Geometric least-squares means (LSMs) are calculated by exponentiating the LSMs from the linear mixed effect model.
Geometric Mean Ratio (GMR) = test/reference
Intra-subject CV % = 100 × (square root (exp[MSE] − 1), where MSE = Residual variance from linear mixed effect model.

The coadministration of 600 mg rifampin with 50 mg mitapivat sulfate decreased the Metabolite exposure relative to when mitapivat sulfate was administered alone. The geometric mean AUC0-t and AUC0-inf ratios of the Metabolite in the presence versus absence of rifampin were 0.37. The geometric mean Cmax ratio of the Metabolite in the presence versus absence of rifampin was 1.2. The intra-subject variability was low at approximately 16% to 18% for AUCs and Cmax.

Conclusions

Total exposure of mitapivat increased in the presence of itraconazole compared to dosing of mitapivat sulfate alone.

Total exposure of mitapivat decreased in the presence of rifampin compared to dosing of mitapivat sulfate alone.

Example 3. Development of a PBPK Model for Mitapivat Sulfate to Evaluate the Potential for Drug-Drug Interactions Part I A physiologically based pharmacokinetic model (hereinafter "PBPK" model) for mitapivat sulfate based on the currently available in-vitro and clinical PK data is being developed. The developed PBPK model will be used to assess DDI liability with mitapivat sulfate acting as a victim of CYP3A4-mediated metabolism as well as a perpetrator of CYP and transporter mediated DDI.

Specifically, a PBPK model that includes a simple first order absorption model will be developed. Full PBPK and minimal PBPK distribution models will be evaluated, both of which consider liver and intestinal metabolism. The fraction of mitapivat sulfate absorbed will be estimated from mass balance data from the [14C] human ADME study (Clinical Study AG348-C-009). In-vitro data will be used to assign the relative contribution of CYP3A4 to the clearance of mitapivat sulfate. $K_I$ and $K_{inact}$ values for mechanism based inhibition of CYP3A4 and CYP3A4 induction (Emax and EC50) data by mitapivat sulfate will be incorporated within the PBPK model to assess the net DDI effects at steady state. Once an mitapivat sulfate PBPK model has been verified against the available clinical data, a series of DDI simulations assessing mitapivat sulfate as a victim or perpetrator of DDI will be performed in healthy volunteers.

Experiments with mitapivat sulfate as a victim

The impact of the co-administration of the strong CYP3A4 inhibitor, itraconazole, on the PK of mitapivat sulfate will be determined based on the following single and multiple-dose administration of 5, 20 and 50 mg BID.

The impact of the co-administration of the strong CYP3A4 inhibitor, ketoconazole, on the PK of mitapivat sulfate will be determined based following single and multiple-dose administration of 5, 20 and 50 mg BID.

The impact of the co-administration of the moderate CYP3A4 inhibitor fluconazole on the PK of mitapivat sulfate will be determined based on the following single and multiple dose administration of 5, 20 and 50 mg BID.

The impact of the co-administration of the mild CYP3A4 inhibitor cimetidine on the PK of mitapivat sulfate will be determined based on the following single- and multiple dose administration of 5, 20 and 50 mg BID.

The impact of the co-administration of the strong CYP3A4 inducer, rifampin, on the PK of mitapivat sulfate will be determined based on the following single and multiple dose administration of 5, 20 and 50 mg BID.

The impact of the co-administration of the moderate CYP3A4 inducer efavirenz on the PK of mitapivat sulfate will be determined following single and multiple dose administration of 5, 20 and 50 mg BID.

Experiments with mitapivat sulfate as perpetrator

The extent to which 5 to 50 mg BID mitapivat sulfate affects the systemic exposure of CYP3A4 substrate midazolam when co-administered with mitapivat sulfate will be determined.

The effect of 5 to 50 mg mitapivat sulfate on the systemic exposures of CYP2B6 substrate bupropion when co-administered will be determined. CYP2B6 induction (Emax and EC50) data by mitapivat sulfate will be incorporated within the PBPK model. Sensitivity analysis will be conducted to gauge the impact of the uncertainty around Emax and EC50 on the predicted DDIs.

The effect of 5 to 50 mg AG mitapivat sulfate BID on the systemic exposures of CYP2C9 substrate warfarin when co-administered will be determined. CYP2C9 induction (Emax and EC50) data by mitapivat sulfate will be incorporated within the PBPK model. Sensitivity analysis will be conducted to gauge the impact of the uncertainty around Emax and EC50 on the predicted DDIs.

The effect of 5 to 50 mg mitapivat sulfate BID on the systemic exposures of CYP2C8/CYP3A4 substrate repaglinide when co-administered will be determined. CYP2C8 induction (Emax and EC50) data by mitapivat sulfate will be incorporated within the PBPK model. Sensitivity analysis will be conducted to gauge the impact of the uncertainty around Emax and EC50 on the predicted DDIs.

The effect of 5 to 50 mg mitapivat sulfate BID on the systemic exposures of CYP2C19 substrate omeprazole when co-administered will be determined. CYP2C19 induction (Emax and EC50) data by mitapivat sulfate will be incorporated within the PBPK model. Sensitivity analysis will be conducted to gauge the impact of the uncertainty around Emax and EC50 on the predicted DDIs.

The effect of mitapivat sulfate (5 to 50 mg BID) on the systemic exposures of OATP1B1/OATP1B3 (rosuvastatin), P-gp (digoxin), metformin (MATE1 and OCT2), OAT3 (methotrexate) substrate drugs when co-administered will be determined. The respective IC50 values for inhibition of OATP1B1, P-gp, MATE1, OCT2 and OAT3 by mitapivat sulfate will be incorporated within the PBPK model. Sensitivity analysis will be performed to assess the impact of these parameters on the DDI liability of mitapivat sulfate.

Part II

The first order absorption component of the previously developed PBPK model will be extended using available pH solubility data to include the ADAM model. The recovery of mitapivat sulfate plasma concentration profiles after single and multiple dosing (up to 50 mg BID) to healthy volunteer subjects will be demonstrated. Once verified against the available clinical data, the modified PBPK model will be used to assess the impact of an increase in gastric pH on the pharmacokinetics of mitapivat sulfate via manipulation of system parameters (gastric pH).

While a number of embodiments have been described, the scope of this disclosure is to be defined by the appended claims, and not by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A method of treating hemolytic anemia in a subject, comprising administering to the subject about 10 mg/day, about 40 mg/day, about 100 mg/day, or about 200 mg/day of mitapivat or a pharmaceutically acceptable salt thereof and a moderate inducer of cytochrome P450 3A4/5 (CYP3A4/5).

2. The method of claim 1, wherein the subject is administered about 10 mg/day of mitapivat or a pharmaceutically acceptable salt thereof.

3. The method of claim 2, wherein the subject is administered about 5 mg of mitapivat or a pharmaceutically acceptable salt thereof twice per day.

4. The method of claim 1, wherein the subject is administered about 40 mg/day of mitapivat or a pharmaceutically acceptable salt thereof.

5. The method of claim 4, wherein the subject is administered about 20 mg of mitapivat or a pharmaceutically acceptable salt thereof twice per day.

6. The method of claim 1, wherein the subject is administered about 100 mg/day of mitapivat or a pharmaceutically acceptable salt thereof.

7. The method of claim 6, wherein the subject is administered about 50 mg of mitapivat or a pharmaceutically acceptable salt thereof twice per day.

8. The method of claim 1, wherein the subject is administered about 200 mg/day of mitapivat or a pharmaceutically acceptable salt thereof.

9. The method of claim 6, wherein the subject is administered about 100 mg of mitapivat or a pharmaceutically acceptable salt thereof twice per day.

10. The method of claim 1, wherein the mitapivat or a pharmaceutically acceptable salt thereof is orally administered as part of a tablet composition.

11. The method of claim 3, wherein the mitapivat or a pharmaceutically acceptable salt thereof is orally administered as part of a tablet composition.

12. The method of claim 5, wherein the mitapivat or a pharmaceutically acceptable salt thereof is orally administered as part of a tablet composition.

13. The method of claim 7, wherein the mitapivat or a pharmaceutically acceptable salt thereof is orally administered as part of a tablet composition.

14. The method of claim 9, wherein the mitapivat or a pharmaceutically acceptable salt thereof is orally administered as part of a tablet composition.

15. The method of claim 10, wherein the tablet composition further comprises microcrystalline cellulose, mannitol, croscarmellose sodium, and sodium stearyl fumarate.

16. The method of claim 11, wherein the tablet composition further comprises microcrystalline cellulose, mannitol, croscarmellose sodium, and sodium stearyl fumarate.

17. The method of claim 12, wherein the tablet composition further comprises microcrystalline cellulose, mannitol, croscarmellose sodium, and sodium stearyl fumarate.

18. The method of claim 13, wherein the tablet composition further comprises microcrystalline cellulose, mannitol, croscarmellose sodium, and sodium stearyl fumarate.

19. The method of claim 14, wherein the tablet composition further comprises microcrystalline cellulose, mannitol, croscarmellose sodium, and sodium stearyl fumarate.

* * * * *

UNITED STATES PATENT AND TRADEMARK OFFICE
CERTIFICATE OF CORRECTION

PATENT NO. : 11,878,049 B1
APPLICATION NO. : 16/900610
DATED : January 23, 2024
INVENTOR(S) : Varsha Venkatachalam Iyer et al.

It is certified that error appears in the above-identified patent and that said Letters Patent is hereby corrected as shown below:

In the Claims

In Column 46, Claim 9, Line 10, replace "The method of claim 6," with -- The method of claim 8, --.

Signed and Sealed this
Twenty-seventh Day of February, 2024

Katherine Kelly Vidal
*Director of the United States Patent and Trademark Office*